(12) United States Patent
Bowers et al.

(10) Patent No.: US 9,987,081 B1
(45) Date of Patent: Jun. 5, 2018

(54) SYSTEMS, DEVICES, AND METHODS FOR SIGNAL GENERATION

(71) Applicant: Iowa Approach, Inc., Menlo Park, CA (US)

(72) Inventors: William Bowers, Westminster, CO (US); Raju Viswanathan, Mountain View, CA (US); Gary Long, Cincinnati, OH (US)

(73) Assignee: Iowa Approach, Inc., Menlo Park, CA (US)

( * ) Notice: Subject to any disclaimer, the term of this patent is extended or adjusted under 35 U.S.C. 154(b) by 0 days. days.

(21) Appl. No.: 15/499,804

(22) Filed: Apr. 27, 2017

(51) Int. Cl.
*A61B 18/10* (2006.01)
*A61B 18/14* (2006.01)
*A61N 1/05* (2006.01)
*A61B 18/12* (2006.01)
*A61B 18/00* (2006.01)

(52) U.S. Cl.
CPC ...... *A61B 18/1482* (2013.01); *A61B 18/1233* (2013.01); *A61N 1/05* (2013.01); *A61B 2018/00577* (2013.01); *A61B 2018/00613* (2013.01); *A61B 2018/00708* (2013.01); *A61B 2018/00988* (2013.01); *A61B 2018/124* (2013.01); *A61B 2018/1407* (2013.01); *A61B 2018/1467* (2013.01)

(58) Field of Classification Search
CPC ........... A61B 2018/00654; A61B 2018/00898; A61B 2018/124
See application file for complete search history.

(56) References Cited

U.S. PATENT DOCUMENTS

| | | | |
|---|---|---|---|
| 4,470,407 | A | 9/1984 | Hussein |
| 5,281,213 | A | 1/1994 | Milder et al. |
| 5,334,193 | A | 8/1994 | Nardella |
| 5,341,807 | A | 8/1994 | Nardella |
| 5,342,301 | A | 8/1994 | Saab |

(Continued)

FOREIGN PATENT DOCUMENTS

| | | |
|---|---|---|
| EP | 1009303 | 6/2009 |
| EP | 2532320 | 12/2012 |

(Continued)

OTHER PUBLICATIONS

Office Action for U.S. Appl. No. 15/201,997, dated Aug. 29, 2017, 12 pages.

(Continued)

*Primary Examiner* — Ronald Hupczey, Jr.
(74) *Attorney, Agent, or Firm* — Cooley LLP

(57) ABSTRACT

Systems, devices, and methods for electroporation ablation therapy are disclosed, with the system including a pulse waveform signal generator for medical ablation therapy that may be coupled to an ablation device including at least one electrode for ablation pulse delivery to tissue. The signal generator may generate and deliver voltage pulses to the ablation device in the form of a pulse waveform in a predetermined sequence where the signal generator may independently configure a set of electrodes of an ablation device. The signal generator may further perform active monitoring of a set of electrode channels and discharge excess energy using the set of electrode channels.

22 Claims, 13 Drawing Sheets

(56) References Cited

U.S. PATENT DOCUMENTS

| | | | |
|---|---|---|---|
| 5,443,463 A * | 8/1995 | Stern | A61B 18/14 606/51 |
| 5,454,370 A | 10/1995 | Avitall | |
| 5,545,161 A | 8/1996 | Imran | |
| 5,617,854 A | 4/1997 | Munsif | |
| 5,624,430 A | 4/1997 | Eton et al. | |
| 5,672,170 A | 9/1997 | Cho | |
| 5,700,243 A | 12/1997 | Narciso, Jr. | |
| 5,702,438 A | 12/1997 | Avitall | |
| 5,706,823 A | 1/1998 | Wodlinger | |
| 5,722,400 A | 3/1998 | Ockuly et al. | |
| 5,779,699 A | 7/1998 | Lipson | |
| 5,788,692 A | 8/1998 | Campbell et al. | |
| 5,810,762 A | 9/1998 | Hofmann | |
| 5,836,874 A | 11/1998 | Swanson et al. | |
| 5,843,154 A | 12/1998 | Osypka | |
| 5,849,028 A | 12/1998 | Chen | |
| 5,868,736 A | 2/1999 | Swanson et al. | |
| 5,871,523 A | 2/1999 | Fleischman et al. | |
| 5,876,336 A | 3/1999 | Swanson et al. | |
| 5,895,404 A | 4/1999 | Ruiz | |
| 5,899,917 A | 5/1999 | Edwards et al. | |
| 5,904,709 A | 5/1999 | Arndt et al. | |
| 5,916,158 A | 6/1999 | Webster, Jr. | |
| 5,921,924 A | 7/1999 | Avitall | |
| 5,928,269 A | 7/1999 | Alt | |
| 5,928,270 A | 7/1999 | Ramsey, III | |
| 6,002,955 A | 12/1999 | Willems et al. | |
| 6,006,131 A | 12/1999 | Cooper et al. | |
| 6,009,351 A | 12/1999 | Flachman | |
| 6,014,579 A | 1/2000 | Pomeranz et al. | |
| 6,029,671 A | 2/2000 | Stevens et al. | |
| 6,033,403 A | 3/2000 | Tu et al. | |
| 6,045,550 A | 4/2000 | Simpson et al. | |
| 6,068,653 A | 5/2000 | LaFontaine | |
| 6,071,281 A | 6/2000 | Burnside et al. | |
| 6,090,104 A | 7/2000 | Webster, Jr. | |
| 6,096,036 A | 8/2000 | Bowe et al. | |
| 6,113,595 A | 9/2000 | Muntermann | |
| 6,119,041 A | 9/2000 | Pomeranz et al. | |
| 6,120,500 A | 9/2000 | Bednarek et al. | |
| 6,146,381 A | 11/2000 | Bowe et al. | |
| 6,164,283 A | 12/2000 | Lesh | |
| 6,167,291 A * | 12/2000 | Barajas | A61B 5/04286 439/909 |
| 6,223,085 B1 | 4/2001 | Dann et al. | |
| 6,231,518 B1 | 5/2001 | Grabek et al. | |
| 6,251,107 B1 | 6/2001 | Schaer | |
| 6,251,128 B1 | 6/2001 | Knopp et al. | |
| 6,270,476 B1 | 8/2001 | Santoianni et al. | |
| 6,272,384 B1 | 8/2001 | Simon et al. | |
| 6,287,306 B1 | 9/2001 | Kroll et al. | |
| 6,314,963 B1 | 11/2001 | Vaska et al. | |
| 6,350,263 B1 * | 2/2002 | Wetzig | A61B 18/1492 600/374 |
| 6,370,412 B1 | 4/2002 | Armoundas et al. | |
| 6,391,024 B1 | 5/2002 | Sun et al. | |
| 6,447,505 B2 | 9/2002 | McGovern et al. | |
| 6,464,699 B1 | 10/2002 | Swanson | |
| 6,470,211 B1 | 10/2002 | Ideker et al. | |
| 6,502,576 B1 | 1/2003 | Lesh | |
| 6,503,247 B2 | 1/2003 | Swartz et al. | |
| 6,517,534 B1 | 2/2003 | McGovern et al. | |
| 6,527,724 B1 | 3/2003 | Fenici | |
| 6,527,767 B2 | 3/2003 | Wang et al. | |
| 6,592,581 B2 | 7/2003 | Bowe | |
| 6,595,991 B2 | 7/2003 | Tollner et al. | |
| 6,607,520 B2 | 8/2003 | Keane | |
| 6,623,480 B1 | 9/2003 | Kuo et al. | |
| 6,638,278 B2 | 10/2003 | Falwell et al. | |
| 6,666,863 B2 | 12/2003 | Wentzel et al. | |
| 6,669,693 B2 | 12/2003 | Friedman | |
| 6,702,811 B2 | 3/2004 | Stewart et al. | |
| 6,719,756 B1 | 4/2004 | Muntermann | |
| 6,723,092 B2 | 4/2004 | Brown et al. | |
| 6,728,563 B2 | 4/2004 | Rashidi | |
| 6,743,225 B2 | 6/2004 | Sanchez et al. | |
| 6,743,239 B1 | 6/2004 | Kuehn et al. | |
| 6,764,486 B2 | 7/2004 | Natale | |
| 6,780,181 B2 | 8/2004 | Kroll et al. | |
| 6,805,128 B1 | 10/2004 | Pless | |
| 6,807,447 B2 | 10/2004 | Griffin, III | |
| 6,892,091 B1 | 5/2005 | Ben-Haim et al. | |
| 6,893,438 B2 | 5/2005 | Hall et al. | |
| 6,955,173 B2 | 10/2005 | Lesh | |
| 6,960,206 B2 | 11/2005 | Keane | |
| 6,960,207 B2 | 11/2005 | Vanney et al. | |
| 6,972,016 B2 | 12/2005 | Hill, III | |
| 6,973,339 B2 | 12/2005 | Govari | |
| 6,979,331 B2 | 12/2005 | Hintringer et al. | |
| 6,984,232 B2 | 1/2006 | Vanney et al. | |
| 6,985,776 B2 | 1/2006 | Kane et al. | |
| 7,001,383 B2 | 2/2006 | Keidar | |
| 7,041,095 B2 * | 5/2006 | Wang | A61B 18/1445 606/32 |
| 7,171,263 B2 | 1/2007 | Darvish et al. | |
| 7,182,725 B2 | 2/2007 | Bonan et al. | |
| 7,195,628 B2 | 3/2007 | Falkenberg | |
| 7,207,988 B2 | 4/2007 | Leckrone et al. | |
| 7,207,989 B2 | 4/2007 | Pike, Jr. et al. | |
| 7,229,402 B2 | 6/2007 | Diaz et al. | |
| 7,229,437 B2 | 6/2007 | Johnson et al. | |
| 7,250,049 B2 | 7/2007 | Roop et al. | |
| 7,285,116 B2 | 10/2007 | de la Rama et al. | |
| 7,285,119 B2 | 10/2007 | Stewart et al. | |
| 7,326,208 B2 | 2/2008 | Vanney et al. | |
| 7,346,379 B2 | 3/2008 | Eng et al. | |
| 7,367,974 B2 * | 5/2008 | Haemmerich | A61B 18/1477 128/898 |
| 7,374,567 B2 | 5/2008 | Heuser | |
| 7,387,629 B2 | 6/2008 | Vanney et al. | |
| 7,387,630 B2 | 6/2008 | Mest | |
| 7,387,636 B2 | 6/2008 | Cohn et al. | |
| 7,416,552 B2 | 8/2008 | Paul et al. | |
| 7,419,477 B2 | 9/2008 | Simpson et al. | |
| 7,419,489 B2 | 9/2008 | Vanney et al. | |
| 7,429,261 B2 | 9/2008 | Kunis et al. | |
| 7,435,248 B2 | 10/2008 | Taimisto et al. | |
| 7,513,896 B2 * | 4/2009 | Orszulak | A61B 18/12 606/32 |
| 7,527,625 B2 | 5/2009 | Knight et al. | |
| 7,578,816 B2 | 8/2009 | Boveja et al. | |
| 7,588,567 B2 | 9/2009 | Boveja et al. | |
| 7,623,899 B2 | 11/2009 | Worley et al. | |
| 7,678,108 B2 | 3/2010 | Chrisitian et al. | |
| 7,681,579 B2 | 3/2010 | Schwartz | |
| 7,771,421 B2 | 8/2010 | Stewart et al. | |
| 7,805,182 B2 | 9/2010 | Weese et al. | |
| 7,850,642 B2 | 12/2010 | Moll et al. | |
| 7,850,685 B2 | 12/2010 | Kunis et al. | |
| 7,857,808 B2 | 12/2010 | Oral et al. | |
| 7,857,809 B2 | 12/2010 | Drysen | |
| 7,869,865 B2 | 1/2011 | Govari et al. | |
| 7,896,873 B2 | 3/2011 | Hiller et al. | |
| 7,917,211 B2 | 3/2011 | Zacouto | |
| 7,918,819 B2 | 4/2011 | Karmarkar et al. | |
| 7,918,850 B2 | 4/2011 | Govari et al. | |
| 7,922,714 B2 | 4/2011 | Stevens-Wright | |
| 7,955,827 B2 | 6/2011 | Rubinsky et al. | |
| 8,048,067 B2 | 11/2011 | Davalos et al. | |
| 8,048,072 B2 | 11/2011 | Verin et al. | |
| 8,100,895 B2 * | 1/2012 | Panos | A61B 18/1492 606/32 |
| 8,100,900 B2 | 1/2012 | Prinz et al. | |
| 8,108,069 B2 | 1/2012 | Stahler et al. | |
| 8,133,220 B2 | 3/2012 | Lee et al. | |
| 8,137,342 B2 | 3/2012 | Crossman | |
| 8,145,289 B2 | 3/2012 | Calabro' et al. | |
| 8,147,486 B2 | 4/2012 | Honour et al. | |
| 8,160,690 B2 | 4/2012 | Wilfley et al. | |
| 8,175,680 B2 | 5/2012 | Panescu | |
| 8,182,477 B2 | 5/2012 | Orszulak et al. | |
| 8,206,384 B2 | 6/2012 | Falwell et al. | |
| 8,206,385 B2 | 6/2012 | Stangenes et al. | |

(56) References Cited

U.S. PATENT DOCUMENTS

| | | |
|---|---|---|
| 8,216,221 B2 | 7/2012 | Ibrahim et al. |
| 8,221,411 B2 | 7/2012 | Francischelli et al. |
| 8,226,648 B2 | 7/2012 | Paul et al. |
| 8,228,065 B2 | 7/2012 | Wirtz et al. |
| 8,235,986 B2 | 8/2012 | Kulesa et al. |
| 8,235,988 B2 | 8/2012 | Davis et al. |
| 8,251,986 B2 | 8/2012 | Chornenky et al. |
| 8,282,631 B2 | 10/2012 | Davalos et al. |
| 8,287,532 B2 | 10/2012 | Carroll et al. |
| 8,414,508 B2 | 4/2013 | Thapliyal et al. |
| 8,430,875 B2 | 4/2013 | Ibrahim et al. |
| 8,433,394 B2 | 4/2013 | Harlev et al. |
| 8,449,535 B2 | 5/2013 | Deno et al. |
| 8,454,594 B2 | 6/2013 | Demarais et al. |
| 8,463,368 B2 | 6/2013 | Harlev et al. |
| 8,475,450 B2 | 7/2013 | Govari et al. |
| 8,486,063 B2 | 7/2013 | Werneth et al. |
| 8,500,733 B2 | 8/2013 | Watson |
| 8,535,304 B2 | 9/2013 | Sklar et al. |
| 8,538,501 B2 | 9/2013 | Venkatachalam et al. |
| 8,562,588 B2 | 10/2013 | Hobbs et al. |
| 8,568,406 B2 | 10/2013 | Harlev et al. |
| 8,571,635 B2 | 10/2013 | McGee |
| 8,571,647 B2 | 10/2013 | Harlev et al. |
| 8,585,695 B2 | 11/2013 | Shih |
| 8,588,885 B2 | 11/2013 | Hall et al. |
| 8,597,288 B2 | 12/2013 | Christian |
| 8,608,735 B2 | 12/2013 | Govari et al. |
| 8,628,522 B2 | 1/2014 | Ibrahim et al. |
| 8,632,534 B2 | 1/2014 | Pearson et al. |
| 8,647,338 B2 | 2/2014 | Chornenky et al. |
| 8,708,952 B2 | 4/2014 | Cohen et al. |
| 8,734,442 B2 | 5/2014 | Cao et al. |
| 8,771,267 B2 | 7/2014 | Kunis et al. |
| 8,795,310 B2 | 8/2014 | Fung et al. |
| 8,808,273 B2 | 8/2014 | Caples et al. |
| 8,834,461 B2 | 9/2014 | Werneth et al. |
| 8,834,464 B2 | 9/2014 | Stewart et al. |
| 8,868,169 B2 | 10/2014 | Narayan et al. |
| 8,876,817 B2 | 11/2014 | Avitall et al. |
| 8,886,309 B2 | 11/2014 | Luther et al. |
| 8,903,488 B2 | 12/2014 | Callas et al. |
| 8,920,411 B2 * | 12/2014 | Gelbart .................. A61B 5/028 606/34 |
| 8,926,589 B2 | 1/2015 | Govari |
| 8,932,287 B2 | 1/2015 | Gelbart et al. |
| 8,945,117 B2 | 2/2015 | Bencini |
| 8,979,841 B2 | 3/2015 | Kunis et al. |
| 8,986,278 B2 | 3/2015 | Fung et al. |
| 9,002,442 B2 | 4/2015 | Harley et al. |
| 9,005,189 B2 | 4/2015 | Davalos et al. |
| 9,005,194 B2 | 4/2015 | Oral et al. |
| 9,011,425 B2 | 4/2015 | Fischer et al. |
| 9,044,245 B2 | 6/2015 | Condie et al. |
| 9,055,959 B2 | 6/2015 | Vaska et al. |
| 9,072,518 B2 | 7/2015 | Swanson |
| 9,078,667 B2 | 7/2015 | Besser et al. |
| 9,101,374 B1 | 8/2015 | Hoch et al. |
| 9,119,533 B2 | 9/2015 | Ghaffari |
| 9,119,634 B2 | 9/2015 | Gelbart et al. |
| 9,131,897 B2 | 9/2015 | Harada et al. |
| 9,155,590 B2 | 10/2015 | Mathur |
| 9,162,037 B2 | 10/2015 | Belson et al. |
| 9,179,972 B2 | 11/2015 | Olson |
| 9,186,481 B2 | 11/2015 | Avitall et al. |
| 9,192,769 B2 | 11/2015 | Donofrio et al. |
| 9,211,405 B2 | 12/2015 | Mahapatra et al. |
| 9,216,055 B2 | 12/2015 | Spence et al. |
| 9,233,248 B2 | 1/2016 | Luther et al. |
| 9,237,926 B2 | 1/2016 | Nollert et al. |
| 9,262,252 B2 | 2/2016 | Kirkpatrick et al. |
| 9,277,957 B2 | 3/2016 | Long et al. |
| 9,282,910 B2 | 3/2016 | Narayan et al. |
| 9,289,258 B2 | 3/2016 | Cohen |
| 9,289,606 B2 | 3/2016 | Paul et al. |
| 9,295,516 B2 | 3/2016 | Pearson et al. |
| 9,301,801 B2 | 4/2016 | Scheib |
| 9,375,268 B2 | 6/2016 | Long |
| 9,414,881 B2 | 8/2016 | Callas et al. |
| 9,468,495 B2 | 10/2016 | Kunis et al. |
| 9,474,574 B2 | 10/2016 | Ibrahim et al. |
| 9,480,525 B2 | 11/2016 | Lopes et al. |
| 9,486,272 B2 | 11/2016 | Bonyak et al. |
| 9,486,273 B2 | 11/2016 | Lopes et al. |
| 9,492,227 B2 | 11/2016 | Lopes et al. |
| 9,492,228 B2 | 11/2016 | Lopes et al. |
| 9,517,103 B2 | 12/2016 | Panescu et al. |
| 9,526,573 B2 | 12/2016 | Lopes et al. |
| 9,532,831 B2 | 1/2017 | Reinders et al. |
| 9,539,010 B2 | 1/2017 | Gagner et al. |
| 9,554,848 B2 | 1/2017 | Stewart et al. |
| 9,700,368 B2 | 7/2017 | Callas et al. |
| 9,724,170 B2 | 8/2017 | Mickelsen |
| 9,757,193 B2 | 9/2017 | Zarins et al. |
| 9,782,099 B2 | 10/2017 | Williams et al. |
| 2001/0007070 A1 | 7/2001 | Stewart et al. |
| 2001/0044624 A1 | 11/2001 | Seraj et al. |
| 2002/0052602 A1 | 5/2002 | Wang et al. |
| 2002/0077627 A1 | 6/2002 | Johnson et al. |
| 2002/0111618 A1 | 8/2002 | Stewart et al. |
| 2002/0169445 A1 | 11/2002 | Jain et al. |
| 2002/0177765 A1 | 11/2002 | Bowe et al. |
| 2002/0183638 A1 | 12/2002 | Swanson |
| 2003/0014098 A1 | 1/2003 | Quijano et al. |
| 2003/0018374 A1 | 1/2003 | Paulos |
| 2003/0050637 A1 | 3/2003 | Maguire et al. |
| 2003/0130598 A1 | 7/2003 | Manning et al. |
| 2003/0130711 A1 | 7/2003 | Pearson et al. |
| 2003/0204161 A1 | 10/2003 | Ferek Petric |
| 2003/0229379 A1 | 12/2003 | Ramsey |
| 2004/0039382 A1 | 2/2004 | Kroll et al. |
| 2004/0049181 A1 | 3/2004 | Stewart et al. |
| 2004/0049182 A1 | 3/2004 | Koblish et al. |
| 2004/0082948 A1 | 4/2004 | Stewart et al. |
| 2004/0087939 A1 | 5/2004 | Eggers et al. |
| 2004/0199157 A1 | 10/2004 | Palanker et al. |
| 2004/0236360 A1 | 11/2004 | Cohn et al. |
| 2004/0254607 A1 | 12/2004 | Wittenberger et al. |
| 2004/0267337 A1 | 12/2004 | Hayzelden |
| 2005/0033282 A1 | 2/2005 | Hooven |
| 2005/0222632 A1 | 10/2005 | Obino |
| 2005/0261672 A1 | 11/2005 | Deem et al. |
| 2006/0009755 A1 | 1/2006 | Sra |
| 2006/0015095 A1 * | 1/2006 | Desinger ............ A61B 18/1477 606/41 |
| 2006/0024359 A1 | 2/2006 | Walker et al. |
| 2006/0142801 A1 | 6/2006 | Demarais et al. |
| 2006/0217703 A1 | 9/2006 | Chornenky et al. |
| 2006/0270900 A1 | 11/2006 | Chin et al. |
| 2006/0287648 A1 | 12/2006 | Schwartz |
| 2006/0293730 A1 | 12/2006 | Rubinsky et al. |
| 2007/0005053 A1 | 1/2007 | Dando |
| 2007/0021744 A1 | 1/2007 | Creighton |
| 2007/0066972 A1 | 3/2007 | Ormsby et al. |
| 2007/0129760 A1 | 6/2007 | Demarais et al. |
| 2007/0156135 A1 | 7/2007 | Rubinsky et al. |
| 2007/0167740 A1 | 7/2007 | Grunewald et al. |
| 2007/0173878 A1 | 7/2007 | Heuser |
| 2007/0208329 A1 | 9/2007 | Ward et al. |
| 2007/0225589 A1 | 9/2007 | Viswanathan |
| 2007/0249923 A1 | 10/2007 | Keenan |
| 2007/0260223 A1 | 11/2007 | Scheibe et al. |
| 2007/0270792 A1 | 11/2007 | Hennemann et al. |
| 2008/0009855 A1 | 1/2008 | Hamou |
| 2008/0033426 A1 | 2/2008 | Machell |
| 2008/0065061 A1 | 3/2008 | Viswanathan |
| 2008/0132885 A1 | 6/2008 | Rubinsky et al. |
| 2008/0161789 A1 | 7/2008 | Thao et al. |
| 2008/0200913 A1 | 8/2008 | Viswanathan |
| 2008/0218322 A1 * | 9/2008 | Shii .................. B60R 25/04 340/426.11 |
| 2008/0243214 A1 | 10/2008 | Koblish |
| 2008/0300574 A1 | 12/2008 | Belson et al. |
| 2008/0300588 A1 | 12/2008 | Groth et al. |

(56) References Cited

U.S. PATENT DOCUMENTS

| | | |
|---|---|---|
| 2009/0024084 A1 | 1/2009 | Khosla et al. |
| 2009/0076500 A1 | 3/2009 | Azure |
| 2009/0105654 A1 | 4/2009 | Kurth et al. |
| 2009/0149917 A1 | 6/2009 | Whitehurst et al. |
| 2009/0163905 A1 | 6/2009 | Winkler et al. |
| 2009/0228003 A1 | 9/2009 | Sinelnikov |
| 2009/0240248 A1 | 9/2009 | Deford et al. |
| 2009/0275827 A1 | 11/2009 | Aiken et al. |
| 2009/0281477 A1 | 11/2009 | Mikus et al. |
| 2009/0306651 A1 | 12/2009 | Schneider |
| 2010/0023004 A1 | 1/2010 | Francischelli et al. |
| 2010/0137861 A1 | 6/2010 | Soroff et al. |
| 2010/0191112 A1 | 7/2010 | Demarais et al. |
| 2010/0191232 A1 | 7/2010 | Boveda |
| 2010/0241185 A1 | 9/2010 | Mahapatra et al. |
| 2010/0261994 A1 | 10/2010 | Davalos et al. |
| 2010/0280513 A1 | 11/2010 | Juergen et al. |
| 2010/0292687 A1 | 11/2010 | Kauphusman et al. |
| 2010/0312300 A1 | 12/2010 | Ryu et al. |
| 2011/0028962 A1 | 2/2011 | Werneth et al. |
| 2011/0098694 A1 | 4/2011 | Long |
| 2011/0106221 A1 | 5/2011 | Neal, II et al. |
| 2011/0130708 A1 | 6/2011 | Perry et al. |
| 2011/0144524 A1 | 6/2011 | Fish et al. |
| 2011/0144633 A1 | 6/2011 | Govari |
| 2011/0160785 A1 | 6/2011 | Mori et al. |
| 2011/0190727 A1 | 8/2011 | Edmunds et al. |
| 2011/0276047 A1 | 11/2011 | Sklar et al. |
| 2011/0276075 A1 | 11/2011 | Fung et al. |
| 2011/0288544 A1 | 11/2011 | Verin et al. |
| 2011/0313417 A1 | 12/2011 | De La Rama et al. |
| 2012/0029512 A1 | 2/2012 | Willard et al. |
| 2012/0053581 A1 | 3/2012 | Wittkampf et al. |
| 2012/0059255 A1 | 3/2012 | Paul et al. |
| 2012/0071872 A1 | 3/2012 | Rubinsky et al. |
| 2012/0089089 A1 | 4/2012 | Swain et al. |
| 2012/0095459 A1 | 4/2012 | Callas et al. |
| 2012/0101413 A1 | 4/2012 | Beetel et al. |
| 2012/0158021 A1 | 6/2012 | Morrill |
| 2012/0165667 A1 | 6/2012 | Altmann et al. |
| 2012/0172867 A1 | 7/2012 | Ryu et al. |
| 2012/0197100 A1 | 8/2012 | Razavi et al. |
| 2012/0209260 A1 | 8/2012 | Lambert et al. |
| 2012/0220998 A1 | 8/2012 | Long et al. |
| 2012/0265198 A1 | 10/2012 | Crow et al. |
| 2012/0283582 A1 | 11/2012 | Mahapatra et al. |
| 2012/0303019 A1 | 11/2012 | Zhao et al. |
| 2012/0310052 A1 | 12/2012 | Mahapatra et al. |
| 2012/0310230 A1 | 12/2012 | Willis |
| 2012/0316557 A1 | 12/2012 | Sartor et al. |
| 2013/0030430 A1 | 1/2013 | Stewart et al. |
| 2013/0060247 A1 | 3/2013 | Sklar et al. |
| 2013/0060248 A1 | 3/2013 | Sklar et al. |
| 2013/0079768 A1 | 3/2013 | De Luca et al. |
| 2013/0090651 A1 | 4/2013 | Smith |
| 2013/0103027 A1 | 4/2013 | Sklar et al. |
| 2013/0103064 A1 | 4/2013 | Arenson et al. |
| 2013/0131662 A1 | 5/2013 | Wittkampf |
| 2013/0158538 A1 | 6/2013 | Govari |
| 2013/0172864 A1 | 7/2013 | Ibrahim et al. |
| 2013/0172875 A1 | 7/2013 | Govari et al. |
| 2013/0184702 A1 | 7/2013 | Neal, II et al. |
| 2013/0226174 A1 | 8/2013 | Ibrahim et al. |
| 2013/0237984 A1 | 9/2013 | Sklar |
| 2013/0253415 A1 | 9/2013 | Sano et al. |
| 2013/0296679 A1 | 11/2013 | Condie et al. |
| 2013/0310829 A1 | 11/2013 | Cohen |
| 2013/0317385 A1 | 11/2013 | Sklar et al. |
| 2013/0331831 A1 | 12/2013 | Werneth et al. |
| 2013/0338467 A1 | 12/2013 | Grasse et al. |
| 2014/0005664 A1 | 1/2014 | Govari et al. |
| 2014/0024911 A1 | 1/2014 | Harlev et al. |
| 2014/0039288 A1 | 2/2014 | Shih |
| 2014/0051993 A1 | 2/2014 | McGee |
| 2014/0052118 A1 | 2/2014 | Laske et al. |
| 2014/0052126 A1 | 2/2014 | Long et al. |
| 2014/0052216 A1 | 2/2014 | Long et al. |
| 2014/0081113 A1 | 3/2014 | Cohen et al. |
| 2014/0100563 A1 | 4/2014 | Govari et al. |
| 2014/0107644 A1 | 4/2014 | Falwell et al. |
| 2014/0142408 A1 | 5/2014 | De La Rama et al. |
| 2014/0163480 A1 | 6/2014 | Govari et al. |
| 2014/0163546 A1 | 6/2014 | Govari et al. |
| 2014/0171942 A1 | 6/2014 | Werneth et al. |
| 2014/0180035 A1 | 6/2014 | Anderson |
| 2014/0194716 A1 | 7/2014 | Diep et al. |
| 2014/0194867 A1 | 7/2014 | Fish et al. |
| 2014/0200567 A1 | 7/2014 | Cox et al. |
| 2014/0235986 A1 | 8/2014 | Harlev et al. |
| 2014/0235989 A1 | 8/2014 | Wodlinger et al. |
| 2014/0243851 A1 | 8/2014 | Cohen et al. |
| 2014/0276760 A1 | 9/2014 | Bonyak et al. |
| 2014/0276782 A1 | 9/2014 | Paskar |
| 2014/0288556 A1 | 9/2014 | Ibrahim et al. |
| 2014/0303721 A1 | 10/2014 | Fung et al. |
| 2014/0343549 A1 | 11/2014 | Spear et al. |
| 2014/0364845 A1 | 12/2014 | Rashidi |
| 2014/0371613 A1 | 12/2014 | Narayan et al. |
| 2015/0005767 A1 | 1/2015 | Werneth et al. |
| 2015/0011995 A1 | 1/2015 | Avitall et al. |
| 2015/0126840 A1 | 5/2015 | Thakur et al. |
| 2015/0133914 A1 | 5/2015 | Koblish |
| 2015/0138977 A1 | 5/2015 | Dacosta |
| 2015/0141978 A1 | 5/2015 | Subramaniam et al. |
| 2015/0142041 A1 | 5/2015 | Kendale et al. |
| 2015/0148796 A1 | 5/2015 | Bencini |
| 2015/0150472 A1 | 6/2015 | Harlev et al. |
| 2015/0157402 A1 | 6/2015 | Kunis et al. |
| 2015/0157412 A1 | 6/2015 | Wallace et al. |
| 2015/0164584 A1 | 6/2015 | Davalos et al. |
| 2015/0173824 A1 | 6/2015 | Davalos et al. |
| 2015/0173828 A1 | 6/2015 | Avitall |
| 2015/0174404 A1 | 6/2015 | Rousso et al. |
| 2015/0182740 A1 | 7/2015 | Mickelsen |
| 2015/0196217 A1 | 7/2015 | Harlev et al. |
| 2015/0223726 A1 | 8/2015 | Harlev et al. |
| 2015/0230699 A1 | 8/2015 | Berul et al. |
| 2015/0258344 A1 | 9/2015 | Tandri et al. |
| 2015/0265342 A1 | 9/2015 | Long et al. |
| 2015/0265344 A1 | 9/2015 | Aktas et al. |
| 2015/0272656 A1 | 10/2015 | Chen |
| 2015/0272664 A9 | 10/2015 | Cohen |
| 2015/0272667 A1 | 10/2015 | Govari et al. |
| 2015/0282729 A1 | 10/2015 | Harlev et al. |
| 2015/0289923 A1 | 10/2015 | Davalos et al. |
| 2015/0304879 A1 | 10/2015 | Dacosta |
| 2015/0320481 A1 | 11/2015 | Cosman et al. |
| 2015/0321021 A1 | 11/2015 | Tandri et al. |
| 2015/0342532 A1 | 12/2015 | Basu et al. |
| 2015/0343212 A1 | 12/2015 | Rousso et al. |
| 2015/0351836 A1 | 12/2015 | Prutchi |
| 2015/0359583 A1 | 12/2015 | Swanson |
| 2016/0008061 A1 | 1/2016 | Fung et al. |
| 2016/0008065 A1 | 1/2016 | Gliner et al. |
| 2016/0029960 A1 | 2/2016 | Toth et al. |
| 2016/0038772 A1 | 2/2016 | Thapliyal et al. |
| 2016/0051204 A1 | 2/2016 | Harlev et al. |
| 2016/0051324 A1 | 2/2016 | Stewart et al. |
| 2016/0058506 A1 | 3/2016 | Spence et al. |
| 2016/0066993 A1 | 3/2016 | Avitall et al. |
| 2016/0074679 A1 | 3/2016 | Thapliyal et al. |
| 2016/0095531 A1 | 4/2016 | Narayan et al. |
| 2016/0095642 A1 | 4/2016 | Deno et al. |
| 2016/0095653 A1 | 4/2016 | Lambert et al. |
| 2016/0100797 A1 | 4/2016 | Mahapatra et al. |
| 2016/0100884 A1 | 4/2016 | Fay et al. |
| 2016/0106498 A1 | 4/2016 | Highsmith et al. |
| 2016/0106500 A1 | 4/2016 | Olson |
| 2016/0113709 A1 | 4/2016 | Maor |
| 2016/0113712 A1 | 4/2016 | Cheung et al. |
| 2016/0120564 A1 | 5/2016 | Kirkpatrick et al. |
| 2016/0128770 A1 | 5/2016 | Afonso et al. |
| 2016/0166167 A1 | 6/2016 | Narayan et al. |
| 2016/0166310 A1 | 6/2016 | Stewart et al. |

(56) References Cited

U.S. PATENT DOCUMENTS

| | | |
|---|---|---|
| 2016/0166311 A1 | 6/2016 | Long et al. |
| 2016/0174865 A1 | 6/2016 | Stewart et al. |
| 2016/0184003 A1 | 6/2016 | Srimathveeravalli et al. |
| 2016/0213282 A1 | 7/2016 | Leo et al. |
| 2016/0220307 A1 | 8/2016 | Miller et al. |
| 2016/0235470 A1 | 8/2016 | Callas et al. |
| 2016/0287314 A1 | 10/2016 | Arena et al. |
| 2016/0310211 A1 | 10/2016 | Long |
| 2016/0324564 A1 | 11/2016 | Gerlach et al. |
| 2016/0324573 A1 | 11/2016 | Mickelsen et al. |
| 2016/0331441 A1 | 11/2016 | Konings |
| 2016/0354142 A1 | 12/2016 | Pearson et al. |
| 2016/0361109 A1 | 12/2016 | Weaver et al. |
| 2017/0035499 A1 | 2/2017 | Stewart et al. |
| 2017/0042449 A1 | 2/2017 | Deno et al. |
| 2017/0042615 A1 | 2/2017 | Salahieh et al. |
| 2017/0056648 A1 | 3/2017 | Syed et al. |
| 2017/0065330 A1 | 3/2017 | Mickelsen et al. |
| 2017/0065339 A1 | 3/2017 | Mickelsen |
| 2017/0065340 A1 | 3/2017 | Long |
| 2017/0065343 A1 | 3/2017 | Mickelsen |
| 2017/0151029 A1 | 6/2017 | Mickelsen |
| 2017/0181795 A1 | 6/2017 | Debruyne |
| 2017/0189097 A1 | 7/2017 | Viswanathan et al. |
| 2017/0215953 A1 | 8/2017 | Long et al. |
| 2017/0245928 A1 | 8/2017 | Xiao et al. |
| 2017/0246455 A1 | 8/2017 | Athos et al. |
| 2017/0312024 A1 | 11/2017 | Harlev et al. |
| 2017/0312025 A1 | 11/2017 | Harlev et al. |
| 2017/0312027 A1 | 11/2017 | Harlev et al. |
| 2018/0001056 A1 | 1/2018 | Leeflang et al. |
| 2018/0042674 A1 | 2/2018 | Mickelsen |
| 2018/0042675 A1 | 2/2018 | Long |
| 2018/0043153 A1 | 2/2018 | Viswanathan et al. |

FOREIGN PATENT DOCUMENTS

| | | |
|---|---|---|
| EP | 2708181 | 3/2014 |
| WO | WO 92/07622 | 5/1992 |
| WO | WO 97/24073 | 7/1997 |
| WO | WO 1999/004851 | 2/1999 |
| WO | WO 1999/022659 | 5/1999 |
| WO | WO 2002/056782 | 7/2002 |
| WO | WO 2012/153928 | 11/2002 |
| WO | WO 2014/031800 | 2/2014 |
| WO | WO 2015/103530 | 7/2015 |
| WO | WO 2015/103574 | 7/2015 |
| WO | WO 2015/171921 | 11/2015 |
| WO | WO 2015/175944 | 11/2015 |
| WO | WO 2015/192018 | 12/2015 |
| WO | WO 2015/192027 | 12/2015 |
| WO | WO 2016/060983 | 4/2016 |
| WO | WO 2017/120169 | 7/2017 |
| WO | WO 2017/192477 | 11/2017 |
| WO | WO 2017/192495 | 11/2017 |
| WO | WO 2017/218734 | 12/2017 |

OTHER PUBLICATIONS

Office Action for U.S. Appl. No. 15/334,646, dated Nov. 16, 2017, 26 pages.
Supplementary European Search Report for European Application No. 15733297.4, dated Aug. 10, 2017, 7 pages.
International Search Report and Written Opinion for International Application No. PCT/US2015/010223, dated Apr. 10, 2015, 19 pages.
International Preliminary Report on Patentability for International Application No. PCT/US2015/010223, dated Jul. 12, 2016, 12 pages.
Office Action for U.S. Appl. No. 14/400,455, dated Mar. 30, 2017, 10 pages.
Office Action for U.S. Appl. No. 15/201,997, dated Apr. 3, 2017, 6 pages.
International Search Report and Written Opinion for International Application No. PCT/US2015/029734, dated Nov. 24, 2015, 15 pages.
International Search Report and Written Opinion for International Application No. PCT/US2015/031086, dated Oct. 21, 2015, 16 pages.
International Search Report and Written Opinion for International Application No. PCT/US2015/055105, dated Mar. 1, 2016, 15 pages.
International Search Report and Written Opinion for International Application No. PCT/US2015/035582, dated Oct. 2, 2015, 17 pages.
International Search Report and Written Opinion for International Application No. PCT/US2015/035592, dated Oct. 2, 2015, 13 pages.
Office Action for U.S. Appl. No. 15/334,646, dated Jul. 25, 2017, 19 pages.
International Search Report and Written Opinion for International Application No. PCT/US2016/057664, dated Feb. 24, 2017, 11 pages.
International Search Report and Written Opinion for International Application No. PCT/US2017/012099, dated May 18, 2017, 17 pages.
Du Pre, B.C. et al., "Minimal coronary artery damage by myocardial electroporation ablation," Europace, 15(1):144-149 (2013).
Hobbs, E. P., "Investor Relations Update: Tissue Ablation via Irreversible Electroporation (IRE)," Powerpoint (2004), 16 pages.
Lavee, J. et al., "A Novel Nonthermal Energy Source for Surgical Epicardial Atrial Ablation: Irreversible Electroporation," The Heart Surgery Forum #2006-1202, 10(2), 2007 [Epub Mar. 2007].
Madhavan, M. et al., "Novel Percutaneous Epicardial Autonomic Modulation in the Canine for Atrial Fibrillation: Results of an Efficacy and Safety Study," Pace, 00:1-11 (2016).
Neven, K. et al., "Safety and Feasibility of Closed Chest Epicardial Catheter Ablation Using Electroporation," Circ Arrhythm Electrophysiol., 7:913-919 (2014).
Neven, K. et al., "Myocardial Lesion Size After Epicardial Electroporation Catheter Ablation After Subxiphoid Puncture," Circ Arrhythm Electrophysiol., 7(4):728-733 (2014).
Neven, K. et al., "Epicardial linear electroporation ablation and lesion size," Heart Rhythm, 11:1465-1470 (2014).
Van Driel, V.J.H.M. et al., "Pulmonary Vein Stenosis After Catheter Ablation Electroporation Versus Radiofrequency," Circ Arrhythm Electrophysiol., 7(4):734-738 (2014).
Van Driel, V.J.H.M. et al., "Low vulnerability of the right phrenic nerve to electroporation ablation," Heart Rhythm, 12:1838-1844 (2015).
Wittkampf, F.H. et al., "Myocardial Lesion Depth With Circular Electroporation Ablation," Circ. Arrhythm Electrophysiol., 5(3):581-586 (2012).
Wittkampf, F.H. et al., "Feasibility of Electroporation for the Creation of Pulmonary Vein Ostial Lesions," J Cardiovasc Electrophysiol, 22(3):302-309 (Mar. 2011).
Office Action for U.S. Appl. No. 15/795,062, dated Dec. 19, 2017, 14 pages.
Office Action for U.S. Appl. No. 15/795,075, dated Feb. 6, 2018, 9 pages.
Office Action for U.S. Appl. No. 15/796,375, dated Jan. 24, 2018, 25 pages.
Office Action for U.S. Appl. No. 15/794,717, dated Feb. 1, 2018, 10 pages.
Office Action for U.S. Appl. No. 15/796,255, dated Jan. 10, 2018, 12 pages.
Office Action for U.S. Appl. No. 15/672,916, dated Feb. 13, 2018, 16 pages.

* cited by examiner

SYSTEMS, DEVICES, AND METHODS FOR SIGNAL GENERATION

BACKGROUND

The generation of pulsed electric fields for tissue therapeutics has moved from the laboratory to the clinic over the past two decades. Application of brief, high DC voltages to tissue may generate locally high electric fields typically in the range of hundreds of volts per centimeter that disrupt cell membranes by generating pores in the cell membrane. While the precise mechanism of this electrically-driven pore generation or electroporation continues to be studied, it is thought that the application of relatively brief and large electric fields generates instabilities in the lipid bilayers in cell membranes, causing the occurrence of a distribution of local gaps or pores in the cell membrane. Such electroporation may be irreversible if the applied electric field at the membrane is larger than a threshold value, leading to the pores remaining open, thereby leading to necrosis and/or apoptosis (cell death). Subsequently, the surrounding tissue may heal naturally.

Electroporation of tissue may be performed using electrode probes coupled to a high voltage generator for generation and delivery of brief, high voltage pulses, and may be limited by the capabilities of the generator. There is hence an unmet need for improved systems, devices, and methods to efficiently generate tissue ablation waveforms for therapeutic treatment, such as for treatment of cardiac arrhythmias, for example.

SUMMARY

Described herein are systems, devices, and methods for ablating tissue through irreversible electroporation. Generally, a system for delivering a pulse waveform to tissue may include a set of electrodes and a signal or voltage waveform generator configured to couple to the set of electrodes during use. The signal generator may include a routing console, a set of electrode channels coupled to the routing console, an energy source coupled to the set of electrode channels, and a processor coupled to the set of electrode channels and to the routing console. In some embodiments, each electrode channel of the set of electrode channels may correspond to an electrode of the set of electrodes. Each electrode channel may include an electronic switch configured to switch between an ON state and an OFF state. In some embodiments, the processor may be configured to selectively define a first sequence of subsets of one or more electrode channels of the set of electrode channels as an anode sequence and to selectively define a second sequence of subsets of one or more electrode channels of the set of electrode channels as a cathode sequence. In some embodiments, the routing console may be configured to selectively couple the set of electrodes during use and include a drive circuit coupled to each electronic switch to control the state of the electronic switch. The processor, the routing console, and the energy source may be collectively configured to deliver a pulse waveform to the set of electrodes in a time-sequenced fashion by pairing respective electrode channels of the first sequence of electrode channels and second sequence of electrode channels.

In some embodiments, the electronic switch of each electrode channel may be a first electronic switch and the drive circuit may be a first drive circuit. Each electrode channel may further include a second electronic switch configured to switch between an ON state and an OFF state, and a second drive circuit coupled to the second electronic switch to control the state of the second electronic switch.

In some embodiments, the processor may be further configured to configure the first sequence as an anode by setting the first electronic switch of the first electrode channel to the ON state and by setting the second electronic switch of the first sequence to the OFF state. The processor may be further configured to configure the second sequence as a cathode by setting the first electronic switch of the second sequence to the OFF state and by setting the second electronic switch of the second sequence to the ON state.

In some embodiments, each of the electronic switches may be selected from the group consisting of bipolar junction transistors, bipolar Field Effect transistors (Bi-FET's), power Metal Oxide Semiconductor Field Effect Transistors (MOSFET's), and Insulated-Gate Bipolar Transistors (IGBT's). In some embodiments, each of the electronic switches may include an insulated-gate bipolar transistor. In some embodiments, the energy source may include a capacitive element. Each electrode channel may further include a resistive element configured to discharge the capacitive element when the energy source is not in use.

In some embodiments, the signal generator may further include a sensing circuit coupled to the set of electrode channels and to the processor. The processor, the routing console and the energy source may be collectively configured to deliver the pulse waveform to the set of electrodes at a first time. The processor and the sensing circuit may be further configured, at a second time prior to the first time and for each electrode channel of the set of electrode channels to conduct a first fault test, including setting the first electronic switch to the ON state, setting the second electronic switch to the OFF state, and classifying that electrode channel as passing the first fault test when substantially no current is detected by the sensing circuit. A second fault test may be conducted and include the steps of setting the first electronic switch to the OFF state, setting the second electronic switch to the ON state, classifying that electrode channel as passing the second fault test when substantially no current is detected by the sensing circuit. A third fault test may be conducted and include the steps of setting the first electronic switch to the ON state, setting the second electronic switch to the ON state, and classifying that electrode channel as passing the third fault test when a predetermined amount of current is detected by the sensing circuit. The electrode channel may be classified as working without fault when that electrode channel passes the first fault test, the second fault test, and the third fault test.

In some embodiments, the signal generator may further include a resistive element coupled to the set of electrode channels, a sensing circuit coupled to the resistive element, the routing console, and to the processor. The processor and the energy source may be collectively configured to deliver the pulse waveform to the set of electrodes at a first time. The processor and the sensing circuit may be further configured, at a second time subsequent to the first time and for each electrode channel of the set of electrode channels to set the first electronic switch to the ON state and set the second electronic switch to the ON state for a predetermined duration of time to at least partially discharge the energy source.

In some embodiments, the signal generator may further include a sensing circuit configured to detect arcing during use. In some embodiments, the system may include an ablation device that includes the set of electrodes as a linear array of N electrodes. The set of electrode channels may include N electrode channels corresponding to the N electrodes. The first sequence of subsets of electrode channels may include an electrode channel corresponding to a first electrode in the linear array of N electrodes. The second sequence of subsets of electrode channels may include only electrode channels that do not correspond to any electrodes adjacent to the first electrode in the linear array of N electrodes.

In some embodiments, a given electrode channel is in the first sequence of subsets at a first time, and is in the second sequence of subsets at a second time subsequent to the first time. In some embodiments, a given subset of electrode channels in the first sequence of subsets and its corresponding subset of electrode channels in the second sequence of subsets may each be configured as a half bridge amplifier. The combination of the given subset of electrode channels and its corresponding subset of electrode channels may be collectively configured as a full bridge amplifier.

In some embodiments, the pulse waveform may include a first level of a hierarchy of the pulse waveform including a first set of pulses, each pulse having a pulse time duration and a first time interval separating successive pulses. The pulse waveform may include a second level of the hierarchy of the pulse waveform including a plurality of first sets of pulses as a second set of pulses, a second time interval separating successive first sets of pulses, the second time interval being at least three times the duration of the first time interval. The pulse waveform may include a third level of the hierarchy of the pulse waveform including a plurality of second sets of pulses as a third set of pulses, a third time interval separating successive second sets of pulses, the third time interval being at least thirty times the duration of the second level time interval.

In some embodiments, the system may include a cardiac stimulator configured to generate a pacing signal for cardiac stimulation during use. The cardiac stimulator may be communicably coupled to the signal generator and further configured to transmit an indication of the pacing signal to the signal generator. The processor of the signal generator may be further configured to generate the pulse waveform in synchronization with the indication of the pacing signal, where the synchronization may include a pre-determined offset.

In some embodiments, the predetermined duration of time may include a set of pulse widths including a first pulse width between about 0.1 $\mu$s and about 1 $\mu$s, a second pulse width between about 1 $\mu$s and about 5 $\mu$s, a third pulse width between about 5 $\mu$s and about 10 $\mu$s, a fourth pulse width between about 10 $\mu$s and about 15 $\mu$s, and a fifth pulse width between about 15 $\mu$s and about 25 $\mu$s. In some embodiments, the processor and the sensing circuit may be further configured to partially discharge the energy source over a plurality of discharge cycles. Each discharge cycle may include partial discharge of each electrode channel of the set of electrode channels. In some embodiments, the processor and the sensing circuit may be further configured to set the predetermined duration of time as: the first pulse width for between about 90 discharge cycles and about 130 discharge cycles; the second pulse width for between about 80 discharge cycles and about 90 discharge cycles; the third pulse width for between about 70 discharge cycles and about 80 discharge cycles; and the fourth pulse width for about 70 discharge cycles or less.

In some embodiments, the system may be used in a method of treating atrial fibrillation in a patient via irreversible electroporation by applying the pulse waveform to the patient.

In some embodiments, a generator described herein may include a routing console configured to couple a set of electrodes during use, a set of electrode channels coupled to the routing console, an energy source coupled to the set of electrode channels, and a processor coupled to the energy source, the set of electrode channels, and the drive circuit. In some embodiments, each electrode channel of the set of electrode channels may correspond to an electrode of the set of electrodes. Each electrode channel may include an electronic switch configured to switch between an ON state and an OFF state, and a drive circuit coupled to the electronic switch to control the state of the electronic switch. In some embodiments, the processor may configure a set of one or more first electrode channels of the set of electrode channels as an anode and set one or more second electrode channels of the set of electrode channels as a cathode. The processor, the routing console, and the energy source may be collectively configured to deliver a pulse waveform to the set of electrodes during use via the one or more first electrode channels and the one or more second electrode channels, and wherein each pulse of the pulse waveform is a substantially DC pulse In some embodiments, the electronic switch of each electrode channel may be a first electronic switch and the drive circuit may be a first drive circuit. Each electrode channel may further include a second electronic switch configured to switch between an ON state and an OFF state, and a second drive circuit coupled to the second electronic switch to control the state of the second electronic switch. In some embodiments, the processor may be further configured to configure each first electrode channel as an anode by setting the first electronic switch of that electrode channel to the ON state and by setting the second electronic switch of the first electrode channel to the OFF state. The processor may further be configured to configure each second electrode channel as a cathode by setting the first electronic switch of that second electrode channel to the OFF state and by setting the second electronic switch of that second electrode channel to the ON state. In some embodiments, each of the electronic switches includes an insulated-gate bipolar transistor. In some embodiments, the energy source may include a capacitive element. Each electrode channel may further include a resistive element configured to discharge the capacitive element when the energy source is not in use.

In some embodiments, the signal generator may further include a sensing circuit coupled to the set of electrode channels and to the processor. The processor and the energy source may be collectively configured to deliver the pulse waveform to the set of electrodes at a first time. The processor and the sensing circuit may be collectively configured, at a second time prior to the first time and for each electrode channel of the set of electrode channels to conduct a first fault test, including setting the first electronic switch to the ON state, setting the second electronic switch to the OFF state, and classifying that electrode channel as passing the first fault test when substantially no current is detected by the sensing circuit. A second fault test may be conducted, including the steps of setting the first electronic switch to the OFF state, setting the second electronic switch to the ON state, and classifying that electrode channel as passing the second fault test when substantially no current is detected by the sensing circuit. A third fault test may be conducted, including the steps of setting the first electronic switch to the ON state, setting the second electronic switch to the ON stat, classifying that electrode channel as passing the third fault test when a predetermined amount of current is detected by the sensing circuit. The electrode channel may be classified as working without fault when that electrode channel passes the first fault test, the second fault test, and the third fault test.

In some embodiments, the signal generator may further include a resistive element coupled to the set of electrode channels, and a sensing circuit coupled to the resistive element and to the processor. The processor and the energy source may be configured to deliver the pulse waveform to the set of electrodes at a first time. The processor and the sensing circuit may be further configured, at a second time subsequent to the first time and for each electrode channel of the set of electrode channels to set the first electronic switch to the ON state and set the second electronic switch to the ON state for a predetermined duration of time to at least partially discharge the energy source.

In some embodiments, each of the electronic switches may include an insulated-gate bipolar transistor. In some embodiments, the energy source may include a capacitive element. Each electrode channel may further include a resistive element configured to discharge the capacitive element when the energy source is not in use. In some embodiments, the signal generator may further include a sensing circuit configured to detect arcing.

In some embodiments, the set of electrode channels including a linear array of N electrode channels. The one or more first electrode channels may correspond to electrode channels in the linear array of N electrode channels. The one or more second electrode channels may not correspond to any electrode channels adjacent to the first electrode channel in the linear array of N electrode channels.

In some embodiments, the processor and the energy source may be collectively configured to deliver the pulse waveform to the set of electrodes at a first time. The processor may be further configured to, at a second time subsequent to the first time configure one of the first electrode channels of the set of electrode channels as a cathode, and configure one of the second electrode channels of the set of electrode channels as an anode. The processor and the energy source may be further collectively configured to deliver the pulse waveform to the set of electrodes at the second time.

In some embodiments, the one or more first electrode channels and the one or more second electrode channels may be configured as a half bridge amplifier. The combination of one or more of the first electrode channels and one or more of the second electrode channels may be collectively configured as a full bridge amplifier.

In some embodiments, the pulse waveform may include a first level of a hierarchy of the pulse waveform including a first set of pulses, each pulse having a pulse time duration, a first time interval separating successive pulses, a second level of the hierarchy of the pulse waveform including a plurality of first sets of pulses as a second set of pulses, a second time interval separating successive first sets of pulses, the second time interval being at least three times the duration of the first time interval, and a third level of the hierarchy of the pulse waveform including a plurality of second sets of pulses as a third set of pulses, a third time interval separating successive second sets of pulses, the third time interval being at least thirty times the duration of the second level time interval.

In some embodiments, the predetermined duration of time includes a set of pulse widths including a first pulse width between about 0.1 µs and about 1 µs, a second pulse width between about 1 µs and about 5 µs, a third pulse width between about 5 µs and about 10 µs, a fourth pulse width between about 10 µs and about 15 µs, and a fifth pulse width between about 15 µs and about 25 µs. In some embodiments, the processor and the sensing circuit may be further configured to partially discharge the energy source over a plurality of discharge cycles. Each discharge cycle may include partial discharge of each electrode channel of the set of electrode channels. In some embodiments, the processor and the sensing circuit are further configured to set the predetermined duration of time as: the first pulse width for between about 90 discharge cycles and about 130 discharge cycles; the second pulse width for between about 80 discharge cycles and about 90 discharge cycles; the third pulse width for between about 70 discharge cycles and about 80 discharge cycles; and the fourth pulse width for about 70 discharge cycles or less.

In some embodiments, the generator may be used in a method of treating atrial fibrillation in a patient via irreversible electroporation by applying the pulse waveform to the patient via the set of electrodes.

Also described herein are methods for signal generation. In general, these methods include the steps of generating configuring a sequence of subsets of one or more electrode channels of a signal generator to act as an anode sequence, configuring a second sequence of subsets of one or more electrode channels of the signal generator as a cathode sequence such that respective electrode channels of the first and second sequences are paired for energy delivery, and delivering, from an energy source, a pulse waveform to a set of electrodes via the paired sequences of electrode channels, and wherein each pulse of the pulse waveform is a substantially DC pulse. In some embodiments, each electrode channel may include an electronic switch configured to switch between an ON state and an OFF state, and a drive circuit coupled to the electronic switch to control the state of the electronic switch In some embodiments, the electronic switch of each electrode channel is a first electronic switch and the drive circuit is a first drive circuit, each electrode channel may further include a second electronic switch configured to switch between an ON state and an OFF state, and a second drive circuit coupled to the second electronic switch to control the state of the second electronic switch. Configuring a first electrode channel as an anode may include setting the first electronic switch of that first electrode channel to the ON state and setting the second electronic switch of that first electrode channel to the OFF state. Configuring a second electrode channel as a cathode includes setting the first electronic switch of that second electrode channel to the OFF state and setting the second electronic switch of that second electrode channel to the ON state. In some embodiments, each electronic switch may include an insulated-gate bipolar transistor. In some embodiments, the method may further include the steps of at least partially discharging, via a resistive element included in each electrode channel, a capacitive element included in the energy source, when the signal generator is not in use.

In some embodiments, the step of delivering the pulse waveform to the set of electrodes occurs at a first time may include additional steps at a second time prior to the first time, for each electrode channel of the set of electrode channels including conducting a first fault test including setting the first electronic switch to the ON state, setting the second electronic switch to the OFF state, and classifying that electrode channel as passing the first fault test when substantially no current is detected in a sensing circuit. A second fault test may be conducted and include the steps of setting the first electronic switch to the OFF state, setting the second electronic switch to the ON state, and classifying that electrode channel as passing the second fault test when substantially no current is detected in the sensing circuit. A third fault test may be conducted and include the steps of setting the first electronic switch to the ON state, setting the second electronic switch to the ON state, classifying that electrode channel as passing the third fault test when a predetermined amount of current is detected in the sensing circuit, and classifying that electrode channel as working without fault when that electrode channel passes the first fault test, the second fault test, and the third fault test.

In some embodiments, the method may include additional steps for each electrode channel of the set of electrode channels including setting the first electronic switch to the ON state and setting the second electronic switch to the ON state for a predetermined duration of time to at least partially discharge the energy source. In some embodiments, the energy source may include a capacitive element and each electrode channel may include a resistive element. The method may further include at least partially discharging, via the resistive element, the capacitive element when the energy source is not in use.

In some embodiments, the set of electrode channels may include a linear array of N electrode channels. The first sequence of subsets of electrode channels may include an electrode channel in the linear array of N electrode channels. The second sequence of subsets of electrode channels may include only electrode channels that do not correspond to any electrode channels adjacent to the first electrode channel in the linear array of N electrode channels.

In some embodiments, the pulse waveform may include a first level of a hierarchy of the pulse waveform including a first set of pulses, each pulse having a pulse time duration, a first time interval separating successive pulses. A second level of the hierarchy of the pulse waveform may include a plurality of first sets of pulses as a second set of pulses, a second time interval separating successive first sets of pulses, the second time interval being at least three times the duration of the first time interval. A third level of the hierarchy of the pulse waveform may include a plurality of second sets of pulses as a third set of pulses, a third time interval separating successive second sets of pulses, the third time interval being at least thirty times the duration of the second level time interval.

In some embodiments, the predetermined duration of time may include a set of pulse widths including a first pulse width between about 0.1 μs and about 1 μs, a second pulse width between about 1 μs and about 5 μs, a third pulse width between about 5 μs and about 10 μs, a fourth pulse width between about 10 μs and about 15 μs, and a fifth pulse width between about 15 μs and about 25 μs.

In some embodiments, the method may include the steps of partially discharging the energy source over a plurality of discharge cycles. Each discharge cycle may include partial discharge of each electrode channel of the set of electrode channels. In some embodiments, the pulse waveform may be applied to a patient in need thereof for treating atrial fibrillation via irreversible electroporation.

In some embodiments, a system described herein may include a set of electrodes and a signal generator configured to couple to the set of electrodes during use. The signal generator may include a routing console and a set of electrode channels coupled to the routing console. Each electrode channel of the set of electrode channels may correspond to an electrode of the set of electrodes. Each electrode channel may include a first electronic switch and a second electronic switch, with both switches configured to switch between an ON state and an OFF state. An energy source may be coupled to the set of electrode channels. A processor may be coupled to the set of electrode channels and to the routing console. The processor may be configured to selectively define a first sequence of subsets of one or more electrode channels of the set of electrode channels as an anode sequence and to selectively define a second sequence of subsets of one or more electrode channels of the set of electrode channels as a cathode sequence. A resistive element may be coupled to the set of electrode channels. A sensing circuit may be coupled to the resistive element, the routing console and to the processor. The routing console may be configured to selectively couple the set of electrodes during use and include a drive circuit coupled to each electronic switch to control the state of the electronic switch. The processor, the routing console, and the energy source collectively may be configured to deliver a pulse waveform to the set of electrodes in a time-sequenced fashion by pairing respective electrode channels of the first sequence of electrode channels and second sequence of electrode channels. At a time subsequent to the pulsed waveform delivery, and for each electrode channel of the set of electrode channels, the first electronic switch may be set to the ON state and the second electronic switch may be set to the ON state for a predetermined duration of time to at least partially discharge the energy source.

DETAILED DESCRIPTION

Figure 1:
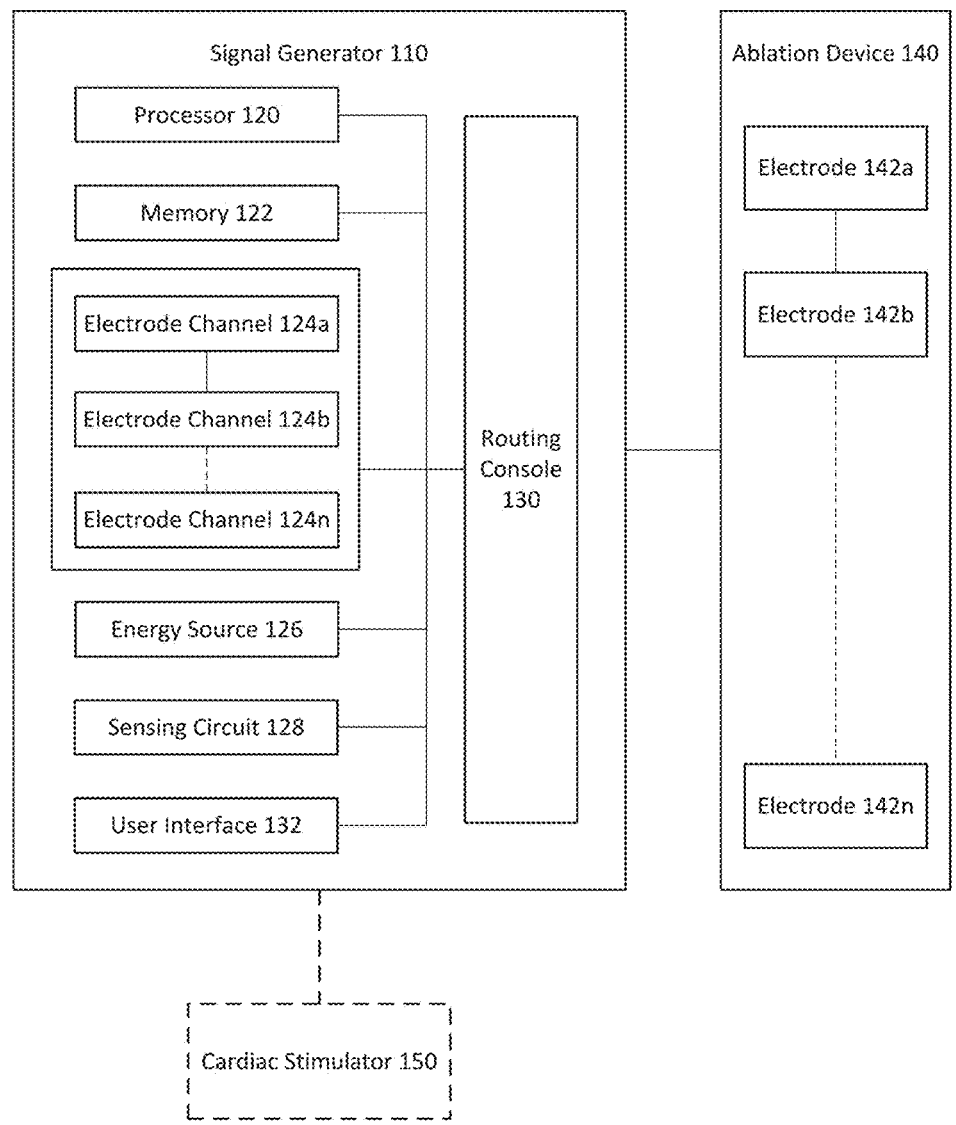
FIG. 1 is a block diagram of an electroporation system, according to embodiments.

Described herein are systems, devices, and methods for signal generation such as for delivery of pulsed electric fields to ablate tissue by irreversible electroporation. Generally, the systems, devices, and methods described herein may be used to generate large electric field magnitudes (e.g., electric fields of about 200 V/cm and above) to treat atrial fibrillation via irreversible electroporation, provide a highly configurable a set of electrode channels (e.g., allow independent and arbitrary electrode selection), deliver energy to one or more ablation devices, provide fault detection to the signal generator, and/or discharge excess stored energy to improve operational speed and reduce treatment time.

A tissue ablation system as described herein may include a signal generator having an energy source, a set of electrode channels, and a processor configured to deliver a voltage pulse waveform to a configurable set of electrode channels to deliver energy to a region of interest. The pulse waveforms disclosed herein may aid in therapeutic treatment of a variety of cardiac arrhythmias (e.g., atrial fibrillation). In order to configure an electrode channel as an anode or cathode, the electrode channel may include a drive circuit coupled to control an electronic switch. For example, an ON/OFF state for a set of electronic switches may be used to configure an electrode channel as an anode or cathode. In some embodiments, the electrode channel may be reconfigured as a cathode or anode for different pulses. The signal generator may include a set of electrode channels that may be coupled to respective electrodes of the same or different ablation device. In some embodiments, each electrode channel may be separately configured as a half-bridge amplifier while a pair of electrode channels may be collectively configured as a full bridge amplifier. As described herein, the number, configuration (e.g., anode, cathode), and operating mode (e.g., monophasic, biphasic) of the electrode channels may be independently controlled. In this manner, the generator may deliver different energy waveforms with different timings synergistically for electroporation of tissue.

In some embodiments, the signal generator may be configured to discharge excess stored energy (e.g., capacitive energy) to ground using the set of electrode channels that deliver pulse waveforms to the set of electrodes. An energy source coupled to the electrode channels may include a capacitive element configured for storing energy. Each electrode channel may include a resistive element configured for discharging the capacitive element when the energy source is not in use (e.g., after applying ablative energy to tissue). For example, an energy source having excess energy stored in a capacitive element (e.g., after delivering a pulse waveform) may sequentially and over a set of cycles discharge a portion of the stored energy through the resistive element in each of the electrode channels until reaching a predetermined threshold. The signal generator may discharge this capacitor energy at faster rate by staggering the discharge period and rest period of each electrode channel.

In some embodiments, the signal generator may perform one or more fault tests to classify a fault status of one or more electrode channels and thereby ensure proper operation of the signal generator. The signal generator may include a sensing circuit configured to detect current through each of the electrode channels. The processor may be configured to set one or more electronic switches of each electrode channel to predetermined states (e.g., test states) to allow the fault status of the electrode channel to be classified. Fault tests may be performed upon powering on the signal generator, such as for a Power on Self-Test (POST) and/or at predetermined intervals during use, such as during tissue ablation energy delivery and capacitor discharge.

The term "electroporation" as used herein refers to the application of an electric field to a cell membrane to change the permeability of the cell membrane to the extracellular environment. The term "reversible electroporation" as used herein refers to the application of an electric field to a cell membrane to temporarily change the permeability of the cell membrane to the extracellular environment. For example, a cell undergoing reversible electroporation may observe the temporary and/or intermittent formation of one or more pores in its cell membrane that close up upon removal of the electric field. The term "irreversible electroporation" as used herein refers to the application of an electric field to a cell membrane to permanently change the permeability of the cell membrane to the extracellular environment. For example, a cell undergoing irreversible electroporation may observe the formation of one or more pores in its cell membrane that persist upon removal of the electric field.

Pulse waveforms for electroporation energy delivery as disclosed herein may enhance the safety, efficiency and effectiveness of energy delivery to tissue by reducing the electric field threshold associated with irreversible electroporation, thus yielding more effective ablative lesions with a reduction in total energy delivered. In some embodiments, the voltage pulse waveforms disclosed herein may be hierarchical and have a nested structure. For example, a pulse waveform may include hierarchical groupings of pulses having associated timescales. In some embodiments, the methods, systems, and devices disclosed herein may comprise one or more of the methods, systems, and apparatuses described in International Application Serial No. PCT/US2016/057664, filed on Oct. 19, 2016, and titled "SYSTEMS, APPARATUSES AND METHODS FOR DELIVERY OF ABLATIVE ENERGY TO TISSUE," the contents of which are hereby incorporated by reference in its entirety.

In some embodiments, the systems may further include a cardiac stimulator used to synchronize the generation of the pulse waveform to a paced heartbeat. The cardiac stimulator may electrically pace the heart with a cardiac stimulator and ensure pacing capture to establish periodicity and predictability of the cardiac cycle. A time window within a refractory period of the periodic cardiac cycle may be selected for voltage pulse waveform delivery. Thus, voltage pulse waveforms may be delivered in the refractory period of the cardiac cycle so as to avoid disruption of the sinus rhythm of the heart. In some embodiments, an ablation device may include one or more catheters, guidewires, balloons, and electrodes. The ablation device may transform into different configurations (e.g., compact and expanded) to position the ablation device within an endocardial space. In some embodiments, the system may optionally include one or more return electrodes.

Generally, to ablate tissue, one or more catheters having one or more electrodes may be advanced in a minimally invasive fashion through vasculature to a target location. In a cardiac application, the electrodes through which a voltage pulse waveform is delivered may be disposed on an epicardial device or on an endocardial device. The methods described here may include configuring a first and second electrode channel of a set of electrode channels as a respective anode and cathode. Each electrode channel may include a drive circuit and an electronic switch configured to switch between ON and OFF states. The drive circuit may be configured to control the state of the electronic switch. A pulse waveform may be delivered to respective electrodes to ablate tissue using the first and second electrode channels. In some embodiments, the pulse waveform may include hierarchical waveforms to aid in tissue ablation and reduce damage to healthy tissue. In some embodiments, the pulse waveform may be generated in synchronization with a pacing signal of the heart to avoid disruption of the sinus rhythm of the heart.

I. Systems

Overview

Disclosed herein are systems and devices configured for tissue ablation via the selective and rapid application of voltage pulse waveforms, resulting in irreversible electroporation. Generally, a system for ablating tissue described herein may include a signal generator and one or more ablation devices having one or more electrodes for the selective and rapid application of DC voltage to drive electroporation. As described herein, the systems and devices may be deployed epicardially and/or endocardially to treat atrial fibrillation. Each ablation device may be coupled to one or more electrode channels of the signal generator. Each electrode channel may be independently configured as an anode or cathode and a voltage pulse waveform may be delivered through one or more of the electrode channels in a predetermined sequence. In some embodiments, the electrode channels may be actively monitored and used for excess energy discharge. In some embodiments, a pacing signal for cardiac stimulation may be generated and used to generate the voltage pulse waveform in synchronization with the pacing signal.

FIG. 1 illustrates an ablation system (100) configured to deliver voltage pulse waveforms for tissue ablation. The system (100) may include a signal generator (110), ablation device (140), and optionally a cardiac stimulator (150). The signal generator (110) may be coupled to at least one ablation device (140), and optionally to the cardiac stimulator (150). The ablation device (140) may include a set of one or more electrodes (142).

Signal Generator

The signal generator (110) may be configured to generate pulse waveforms for irreversible electroporation of tissue, such as, for example, heart tissue. The signal generator (110) may be a voltage pulse waveform generator and deliver a pulse waveform to a set of electrodes (142a, 142b, . . . , 142n) of the ablation device (140). The signal generator (110) may generate and deliver several types of signals including, but not limited to, radiofrequency (RF), direct current (DC) impulses (such as high-voltage, ultra-short pulses used in electroporation), stimulus range impulses, and/or hybrid electrical impulses. For example, the signal generator (110) may generate monophasic (DC) pulses and biphasic (DC and AC) pulses. The signal generator (110) may include a processor (120), memory (122), a set of electrode channels (124a, 124b, . . . , 124n), energy source (126), sensing circuit (128), routing console (130), and user interface (132). One or more signal generator components may be coupled using a communication bus. The processor (120) may incorporate data received from one or more of memory (122), electrode channels (124), energy source (126), sensing circuit (128), routing console (130), user interface (132), ablation device (140), and cardiac stimulator (150) to determine the parameters (e.g., amplitude, width, duty cycle, timing, etc.) of the voltage pulse waveform to be generated by the signal generator (110). The memory (122) may further store instructions to cause the processor (120) to execute modules, processes and/or functions associated with the system (100), such as pulse waveform generation and delivery, electrode channel configuration, fault testing, energy discharge, and/or cardiac pacing synchronization. For example, the memory (122) may be configured to store anode/cathode configuration data, electrode channel configuration data, pulse waveform data, fault data, energy discharge data, heart pacing data, patient data, clinical data, procedure data, and/or the like.

In some embodiments, the ablation device (140) may include a catheter configured to receive and/or deliver the pulse waveforms described herein. For example, the ablation device (140) may be introduced into an endocardial space of the left atrium and positioned to align one or more electrodes (142a, 142b, . . . , 142n) to heart tissue (e.g., one or more pulmonary vein ostia of the left atrium), and then deliver the pulse waveforms to ablate tissue. In another example, the ablation devices (140) may ablate tissue using an epicardial approach. The ablation device (140) may include one or more electrodes (142a, 142b, . . . , 142n), which may, in some embodiments, be a set of independently addressable electrodes. For example, the electrodes (142a, 142b, . . . , 142n) may be grouped into one or more anode-cathode subsets such as, for example, a subset including one anode and one cathode, a subset including two anodes and two cathodes, a subset including two anodes and one cathode, a subset including one anode and two cathodes, a subset including three anodes and one cathode, a subset including three anodes and two cathodes, and/or the like. The set of electrodes (142) may include any number of electrodes, for example, 2, 3, 4, 5, 6, 7, 8, 9, 10, 12, 14, 16, 18, 20, or more electrodes. In some embodiments, the methods, systems, and devices disclosed herein may comprise one or more of the methods, systems, and devices described in International Application Serial No. PCT/US17/12099, filed on Jan. 4, 2017, and titled "SYSTEMS, DEVICES, AND METHODS FOR DELIVERY OF PULSED ELECTRIC FIELD ABLATIVE ENERGY TO ENDOCARDIAL TISSUE," and International Application Serial No. PCT/US2013/031252, filed on Mar. 14, 2013, and titled "CATHETERS, CATHETER SYSTEMS, AND METHODS FOR PUNCTURING THROUGH A TISSUE STRUCTURE AND ABLATING A TISSUE REGION," the contents of which are hereby incorporated by reference in its entirety.

In some embodiments, the processor (120) may be any suitable processing device configured to run and/or execute a set of instructions or code and may include one or more data processors, image processors, graphics processing units, physics processing units, digital signal processors, and/or central processing units. The processor (120) may be, for example, a general purpose processor, Field Programmable Gate Array (FPGA), an Application Specific Integrated Circuit (ASIC), and/or the like. The processor (120) may be configured to run and/or execute application processes and/or other modules, processes and/or functions associated with the system and/or a network associated therewith (not shown). In some embodiments, the processor may comprise both a microcontroller unit and an FPGA unit, with the microcontroller sending electrode sequence instructions to the FPGA. The underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, and/or the like.

In some embodiments, the memory (122) may include a database (not shown) and may be, for example, a random access memory (RAM), a memory buffer, a hard drive, an erasable programmable read-only memory (EPROM), an electrically erasable read-only memory (EEPROM), a read-only memory (ROM), Flash memory, etc. The memory (122) may store instructions to cause the processor (120) to execute modules, processes and/or functions associated with the system (100), such as pulse waveform generation, electrode channel configuration, fault detection, energy discharge, and/or cardiac pacing.

In some embodiments, a set of electrode channels (124) may include a set of active solid-state switches. The set of electrode channels (124) may be configured in a number of ways, including independent anode/cathode configuration for each electrode channel. For example, the electrode channels (124a, 124b, . . . , 124n) may be grouped into one or more anode-cathode subsets such as, for example, a subset including one anode and one cathode, a subset including two anodes and two cathodes, a subset including two anodes and one cathode, a subset including one anode and two cathodes, a subset including three anodes and one cathode, a subset including three anodes and two cathodes, and/or the like. The set of electrode channels (124) may include any number of channels, for example, 2, 3, 4, 5, 6, 7, 8, 9, 10, 12, 14, 16, 18, 20, or more electrode channels. Energy delivery may use any combination of electrode channels (124) and any order for an energy delivery sequence. The energy delivered may be an RF and/or any tissue ablation energy. In some embodiments, the set of electrode channels may provide a discharge path to ground (e.g., capacitor discharge) for excess energy of an energy source (126). In some of these embodiments, excess energy may be discharged through the set of electrode channels (124) such that the signal generator (110) does not include a separate bleeder resistor and/or dump circuit, thereby reducing components count, generator size, cost, and/or manufacturing complexity.

The set of electrode channels (124) may be coupled to a routing console (130) to deliver energy to a set of electrodes (142) coupled to the routing console (130). The set of electrode channels (124) may be coupled to an energy source (126) to receive energy (e.g., a pulse waveform). Processor (120) may be coupled to each electrode channel (124) to configure an anode/cathode configuration for each electrode channel (124), which may be configured on a per pulse basis, per operator input, and/or the like. The processor (120) and energy source (126) may be collectively configured to deliver a pulse waveform to the set of electrodes (142) through the set of electrode channels (124). In some embodiments, each electrode channel (124) may include an electronic switch (e.g., bipolar transistor) and a drive circuit, as described in detail herein. In some embodiments, each electrode channel (124) may have a bootstrap configuration for low and high frequency operation. For example, the pulse duration of voltage pulses delivered through an electrode channel may be in the range of between about 1 microsecond and about 1000 microseconds. In biphasic mode, this corresponds to an approximate frequency range of between about 500 Hz and about 500 KHz for the frequency associated with the voltage pulses.

In some embodiments, an energy source (126) may be configured to convert and supply energy to a set of electrodes (142) coupled to the signal generator (110). The energy source (126) of the signal generator (110) may include a DC power supply and be configured as an AC/DC switcher. In some embodiments, an energy source (126) of the signal generator (110) may deliver rectangular-wave pulses with a peak maximum voltage of about 7 kV into a device with an impedance in the range of about 30Ω to about 3000Ω for a maximum duration of about 1000 μs. Pulses may be delivered in bursts, such as for example, in a sequence of between about 2 pulses and about 10 pulses interrupted by pauses of between about 1 ms and about 1000 ms. In one embodiment, the energy source may deliver about a 3 kV pulse at about 150 A. In some of these embodiments, the energy source (126) may be configured to store energy. For example, the energy source (126) may include one or more capacitors to store energy from a power supply. While these examples are included for purely non-limiting illustrative purposes, it is noted that a variety of pulse waveforms with a range of pulse durations, intervals between pulses, pulse groupings, etc. may be generated depending on the clinical application.

In some embodiments, a sensing circuit (128) may be configured to determine an amount of current being delivered to a device coupled to the signal generator (110) (e.g., electrode (142) coupled to the electrode channel (124)). As described in more detail herein, the sensing circuit (128) may also be used to classify an electrode channel fault, monitor capacitor discharge, and/or sense arcing. In some embodiments, the sensing circuit (128) may be a direct current sensing circuit and/or a low-side sensing circuit. The sensing circuit may include one or more operational amplifiers, difference amplifiers (DA), instrumentation amplifiers (IA), and/or current shunt monitors (CSM).

In some embodiments, the routing console (130) may be configured to electrically couple a set of electrodes (142) of an ablation device (140) to a set of electrode channels (124). The routing console (130) may be configured to selectively deliver energy to the set of electrodes (142) using the set of electrode channels (124). One or more ablation devices (140) each having a set of electrodes (142) may be coupled to the routing console (130). The set of electrodes (142) may include any number of electrodes, for example, 1, 2, 3, 4, 5, 6, 7, 8, 9, 10, 12, 14, 16, 18, 20, or more electrodes.

In some embodiments, the electrode channels (124) configured for energy delivery (e.g., configured as an anode/cathode pair of electrode channels) may not be adjacent to each other. For example, the set of electrode channels (124) may include a set of N electrode channels (124n) in a linear array. In one embodiment, a first electrode channel may correspond to a first electrode channel (124a) in the linear array of N electrode channels (124n). One or more of a second and third electrode channel (124b, 124c) may not be adjacent to the first electrode channel (124a) in the linear array of N electrode channels (124n).

Figure 5:
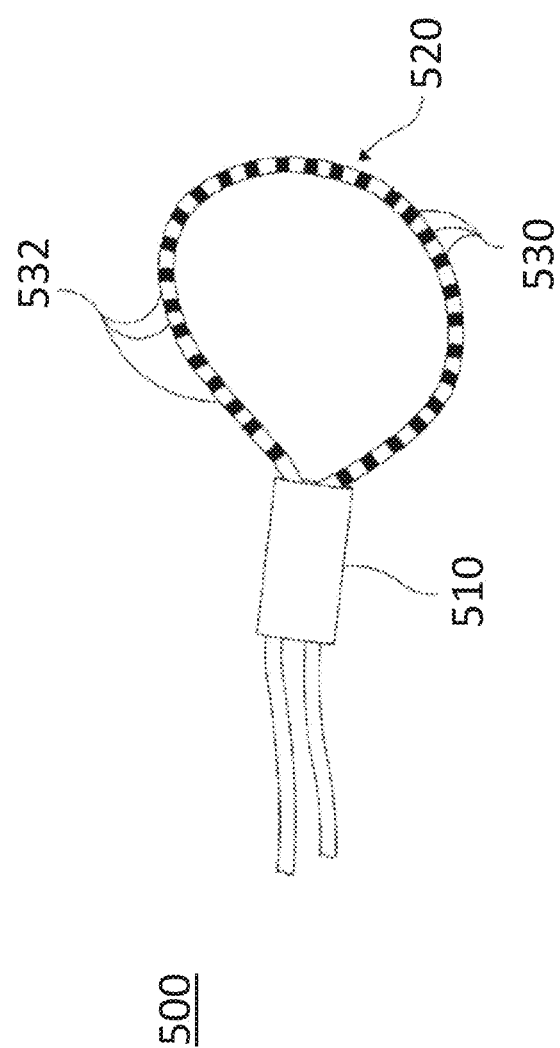
FIG. 5 is a partial close-up view of a central portion of an ablation catheter, according to other embodiments.

A multi-electrode ablation device may allow targeted and precise energy delivery to tissue. In some embodiments, the electrodes (142) of an ablation device (140) may be configured for energy delivery (e.g., as an anode/cathode pair of electrodes (142)) and may be adjacent to each other within a linear array of the electrodes (142) in the ablation device (140). For example, an ablation device (140) may include a set of electrodes (142) as a linear array of N electrodes (142n). As discussed in more detail herein, FIG. 5 illustrates another embodiment of an ablation device (500) including a linear array of electrodes (530). The signal generator (110) coupled to the ablation device (140) may include a set of electrode channels (124) having N electrode channels (124n) corresponding to the N electrodes (142n) of the ablation device (140). In one embodiment, the first electrode channel (124a) of the N electrode channels (124n) may correspond to a first electrode (142a) in the linear array of N electrodes (142n). One or more of second and third electrode channel (124b, 124c) of the N electrode channels (124n) may not correspond to any of the electrodes adjacent to the first electrode (142a) in the linear array of N electrodes (142n).

Configurable electrode channel and electrode selection may provide flexibility in positioning the electrodes for ablating a desired region of interest. In one embodiment, the routing console (130) may couple to a set of 16 electrodes (142) of an ablation device (140). The routing console (130) may receive input from the processor (120) and/or user interface (132) for electrode channel selection and energy delivery to one or more electrodes (142). Additionally or alternatively, the routing console (130) may couple to a cardiac stimulator (150) and be configured to receive data from devices (e.g., heart pacing data from a pacing device) used for synchronization of a pulse waveform with a patient cardiac cycle.

In some embodiments, a user interface (132) may be configured as a communication interface between an operator and the system (100). The user interface (132) may include an input device and output device (e.g., touch surface and display). For example, patient data from memory (122) may be received by user interface (132) and output visually and/or audibly. Electric current data from sensing circuit (128) may be received and output on a display of user interface (132). As another example, operator control of an input device having one or more buttons, knobs, dials, switches, trackball, touch surface, and/or the like, may generate a control signal to the signal generator (110) and/or ablation device (140).

In some embodiments, an input device of the user interface (132) may include a touch surface for operator input and may be configured to detect contact and movement on the touch surface using any of a plurality of touch sensitivity technologies including capacitive, resistive, infrared, optical imaging, dispersive signal, acoustic pulse recognition, and surface acoustic wave technologies. Additionally or alternatively, the user interface (132) may include a step switch or foot pedal.

In some embodiments, an output device of the user interface (132) may include one or more of a display device and audio device. The display device may include at least one of a light emitting diode (LED), liquid crystal display (LCD), electroluminescent display (ELD), plasma display panel (PDP), thin film transistor (TFT), and organic light emitting diodes (OLED). An audio device may audibly output patient data, sensor data, system data, other data, alarms, warnings, and/or the like. The audio device may include at least one of a speaker, piezoelectric audio device, magnetostrictive speaker, and/or digital speaker. In one embodiment, the audio device may output an audible warning upon detection of a fault in the signal generator (110).

In some embodiments, the signal generator (110) may be mounted on a trolley or cart. In some embodiments, the user interface (132) may be formed in the same or different housing as the signal generator (110). The user interface (132) may be mounted to any suitable object, such as furniture (e.g., a bed rail), a wall, a ceiling, or may be self-standing. In some embodiments, the input device may include a wired and/or wireless transmitter configured to transmit a control signal to a wired and/or wireless receiver of the signal generator (110).

In some embodiments, a cardiac stimulator (150) including a pacing device may be configured to generate a heart pacing signal to be delivered to a patient via the pacing device. An indication of the pacing signal may be transmitted by the cardiac stimulator (150) to the signal generator (110). Based on the pacing signal, an indication of a voltage pulse waveform may be selected, computed, and/or otherwise identified by the processor (120) and generated by the signal generator (110). In some embodiments, the signal generator (110) may be configured to generate the voltage pulse waveform in synchronization with the indication of the pacing signal (e.g., within a common refractory window). For example, in some embodiments, the common refractory window may start substantially immediately following a ventricular pacing signal (or after a very small delay) and last for a duration of between about 150 ms and about 250 ms thereafter. In such embodiments, an entire pulse waveform may be delivered within this duration. Heart pacing is described further herein with respect to FIG. 13.

In some embodiments, the systems described herein may include one or more sterile coverings configured to create a sterile barrier around portions of the system (100). In some embodiments, the system (100) may include one or more sterile coverings to form a sterile field. For example, a sterile covering may be placed between the ablation device(s) and the patient, forming a barrier between an interior, non-sterile side including the patient, signal generator, and ablation devices and an exterior, sterile side including the operator. Additionally or alternatively, components of the system (100) may be sterilizable. The sterile covering may include, for example, a sterile drape configured to cover at least a portion of a system component. In one embodiment, a sterile covering (e.g., sterile drape) may be configured to create a sterile barrier with respect to a user interface (132) of the system (100). The sterile drape may be clear and allow an operator to visualize and manually manipulate the user interface (132). The sterile covering may conform tightly around one or more system components or may drape loosely so as to allow components to be adjusted within the sterile field.

Figure 2:
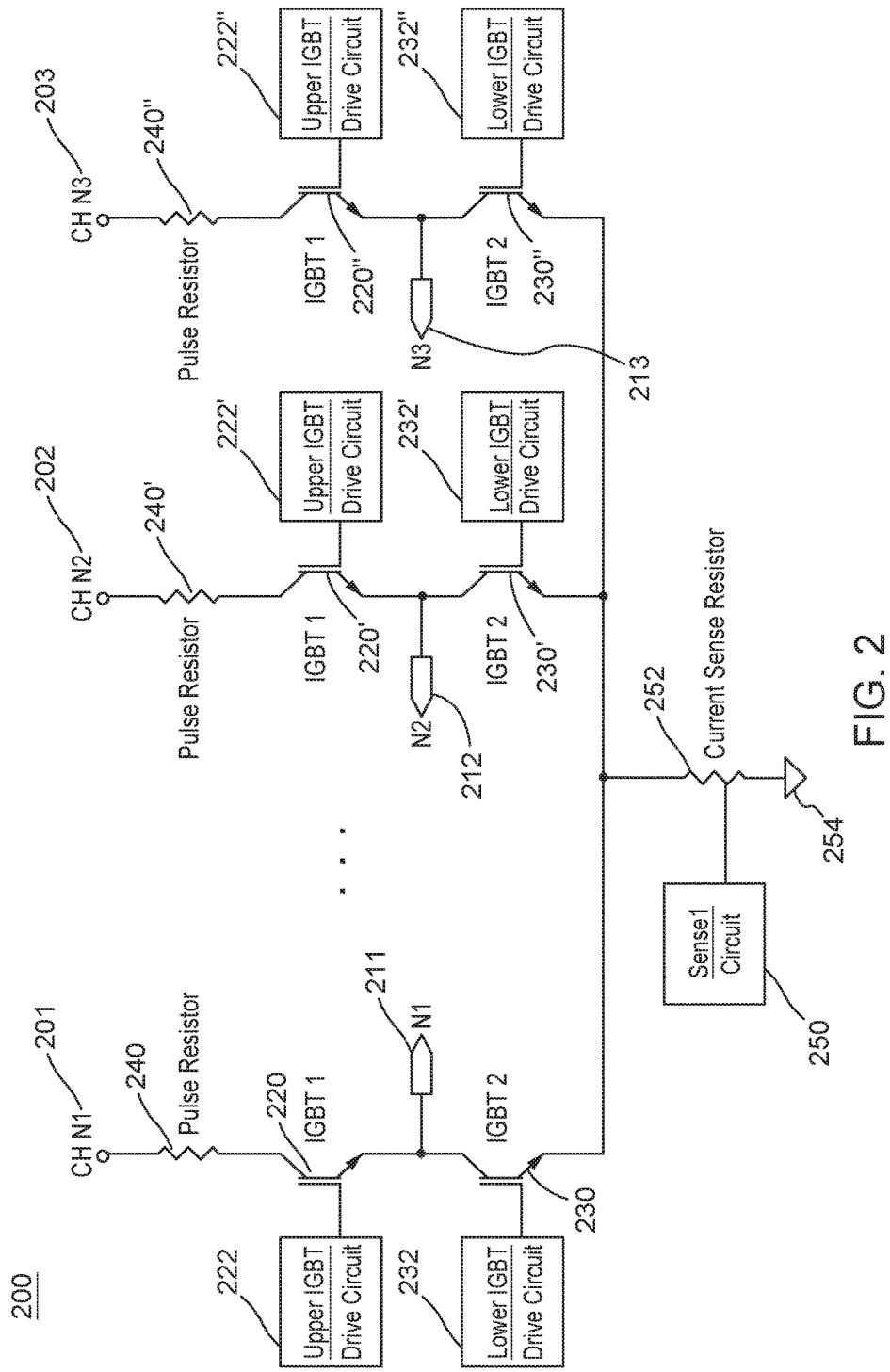
FIG. 2 is a circuit diagram of a signal generator, according to embodiments.

FIG. 2 illustrates a circuit diagram of an embodiment of a signal generator (200) that may be structurally and/or functionally similar to signal generator (110). The signal generator (200) may include one or more electrode channels (201, 202, 203). FIG. 2 illustrates each of the electrode channels having a similar circuit configuration that may be structurally and/or functionally similar to the electrode channels (124a, 124b, ..., 124n). In some embodiments, each of the electrodes channels (201, 202, 203) may be configured individually as a half bridge amplifier while a pair of the electrode channels may be collectively configured as a full bridge amplifier. The signal generators as described herein may include a flexibly programmable electrode configuration; various subsets of electrodes may be configured as anodes and cathodes dynamically and rapidly. Thus, in an ablation energy delivery process, energy may be delivered rapidly over a sequence of paired electrode subsets. In some cases, a given electrode may be configured as an anode, and shortly thereafter as a cathode, during the course of sequencing over a succession of paired electrode subsets. Likewise, a biphasic waveform may also be delivered with the help of this topology, where an initially given anode-cathode pair may be made to reverse polarity after a very brief switching time interval; repeatedly alternating the sequencing of anode/cathode selection may yield a biphasic or AC voltage pulse train. The signal generator (200) may include N number of electrode channels, for example, 1, 2, 3, 4, 5, 6, 7, 8, 9, 10, 12, 14, 16, 18, 20, or more electrode channels. Described with reference to the first electrode channel (201) for the sake of simplicity, each electrode channel may include a first electronic switch (220) configured to switch between an ON state and an OFF state. A first drive circuit (222) may be coupled to the gate terminal of the first electronic switch (220) to control the state of the first electronic switch (220). The first electrode channel (201) further includes a second electronic switch (230) configured to switch between an ON and an OFF state. A second drive circuit (232) may be coupled to the gate terminal of the second electronic switch (230) to control the state of the second electronic switch (230). Each of the drive circuits (222, 232) may be coupled to and controlled by a processor (e.g., processor (120)). An output channel (211) may be coupled to the emitter terminal of the first electronic switch (220) and to the collector terminal of the second electronic switch (230), and may form part of a current path for electrical currents to pass via electrodes on a medical device (not shown) through an electrical load (such as patient anatomy) to one or more output channels coupled to a second electrode channel as described below. The output channel (211) may be coupled to a first electrode such as a first electrode 142(a) of ablation device (140).

Likewise, second and third electrode channels (202, 203) may include respective first electronic switches (220', 220"), each configured to switch between an ON state and an OFF state. First drive circuits (222', 222") may be coupled to respective first electronic switches (220', 220") to control the state of the first electronic switches (220', 220"). Output channels (212, 213) may be coupled between the emitter terminals of the first electronic switches (220', 220") and the collector terminals of the second electronic switches (230', 230"). The output channels (212, 213) may be coupled to respective second and third electrodes, such as the second electrode (142b) and the third electrode (142c) of ablation device (140). The second and third electrode channels (202, 203) further include respective second electronic switches (230', 230") configured to switch between an ON and an OFF state. Second drive circuits (232', 232") may be coupled to the gate terminals of the second electronic switches (230', 230") to control the state of the second electronic switches (230', 230"). Each of the drive circuits (222', 222", 232', 232") may be coupled to and controlled by a processor (e.g., processor (120)). The drive circuits controlled by the processor effectively comprise the routing console 130. As described above, the routing console may be configured to couple to a set of device electrodes connected to the output channels. Each electrode channel (201, 202, . . . ) corresponds to a respective electrode (142a, 142b, . . . ) of the set of device electrodes. As an exemplary illustration of waveform delivery, if switches (220, 230) are respectively in ON and OFF states, switches (220', 230') are respectively in OFF and ON states, and switches (220" and 230" are respectively in OFF and ON states, and all other switches of all other electrode channels are in an OFF state, a positive voltage pulse is delivered with output channel N (211) as anode or positive terminal and with output channels N+3 (212 in FIG. 2) and N+4 (213 in FIG. 2) as cathodes or negative/ground terminals. The duration of the ON state of the switches determines the time width of the pulse. In this manner a sequence of pulses may be delivered over any sequence of anode-cathode pairings, including repeated pulsing of a given or particular anode-cathode combination. Waveform delivery may be interspersed over a sequence of electrodes with the architecture of the generator disclosed herein. While the example of electrode channel selection disclosed in the foregoing described the selection of one anode channel and two cathode channels, it should be clear that a variety of such anode-cathode combinations may be selected without limitation.

The electronic switches (220-220", 230-230", 320-320", 330-330") as described herein may include one or more bipolar transistors, such as bipolar junction transistors or Bipolar Field Effect Transistors. In some embodiments, one or more of the electronic switches include insulated-gate bipolar transistors (IGBT's). Such IGBT switches may be capable of handling the high instantaneous power associated with high voltages, in the approximate range of about 50,000 W to about 300,000 W. An energy source (not shown) may be coupled to the collector terminals of the first electronic switches (220, 220', 220") of the electrode channels (201, 202, 203) through respective resistive elements (240, 240', 240"). As described herein in more detail, the resistive elements (240, 240', 240") may each be configured to discharge a capacitive element of the energy source when the energy source is not in use. In some embodiments, the resistive element may have a resistance in the range of between about 5 Ohms and about 25 Ohms. Each of the electrode channels (201, 202, 203) may be coupled to a sensing circuit (250) and current sense resistor (252). In some embodiments, the sensing circuit (250) may be configured to detect arcing during use. In FIG. 2, the sensing circuit (250) may be coupled between the emitter terminal of the second electronic switches (230, 230', 230") and ground (254). Additionally or alternatively, each electrode channel (201, 202, 203) may be coupled to a respective sensing circuit (250) and current sense resistor (252).

In some embodiments, as described with respect to FIGS. 1 and 2, a processor such as processor (120) coupled to the set of drive circuits (222, 232) may configure the first electrode channel (201) as an anode. One or more of the second and third electrode channels (202, 203) may similarly be configured by the processor (120) as a cathode. In one embodiment, the first electrode channel (201) may be configured as an anode by setting the first electronic switch (220) of the first electrode channel (201) to the ON state and by setting the second electronic switch (230) of the first electrode channel (201) to the OFF state. Each of the second and third electrode channels (202, 203) may be configured as a cathode by setting their respective first electronic switches (220', 220") to the OFF state and setting their respective second electronic switches (230', 230") to the ON state. In this manner, the electrode channels (201, 202) may, for example, form a current path to a tissue site (e.g., coupled to each of the output channels (211, 212) using the first electronic switch (220) of the first electrode channel (201) and second electronic switch (230') of the second electrode channel (202).

The processor (120) and energy source (126) may be collectively configured to deliver a pulse waveform to the set of electrodes during use via one or more of the electrode channels (201, 202, 203). The signal generator (200) may deliver biphasic (AC) pulses where in some embodiments, after delivering a voltage pulse to the set of output channels (211, 212, 213) with output channels (211) as an anode and output channels (212, 213) as cathodes, the polarities are immediately reversed and a voltage pulse of opposite polarity is then delivered with output channel (211) as a cathode and output channels (212, 213) as anodes, and so on until a desired number of biphasic pulses has been delivered to the output channel set (211, 212, 213) in the form of a suitable waveform. Subsequently (and possibly with a programmable time interval), a different set of device electrodes (or output channels) may be configured as anodes and cathodes, and the waveform may be delivered again over this new set of device electrodes. In this manner, the voltage waveform may be sequenced over any desired collection of electrodes. Generally, the processor (120) and energy source (126) may be collectively configured to deliver the pulse waveform over a sequenced set of electrodes (142a, 142b, . . . , 142n).

In some embodiments, as described in more detail herein, the pulse waveform delivered using the signal generator (200) may include a set of levels of a hierarchy and/or may be in synchronization with the indication of a pacing signal generated from a cardiac stimulator (150).

Figure 3:
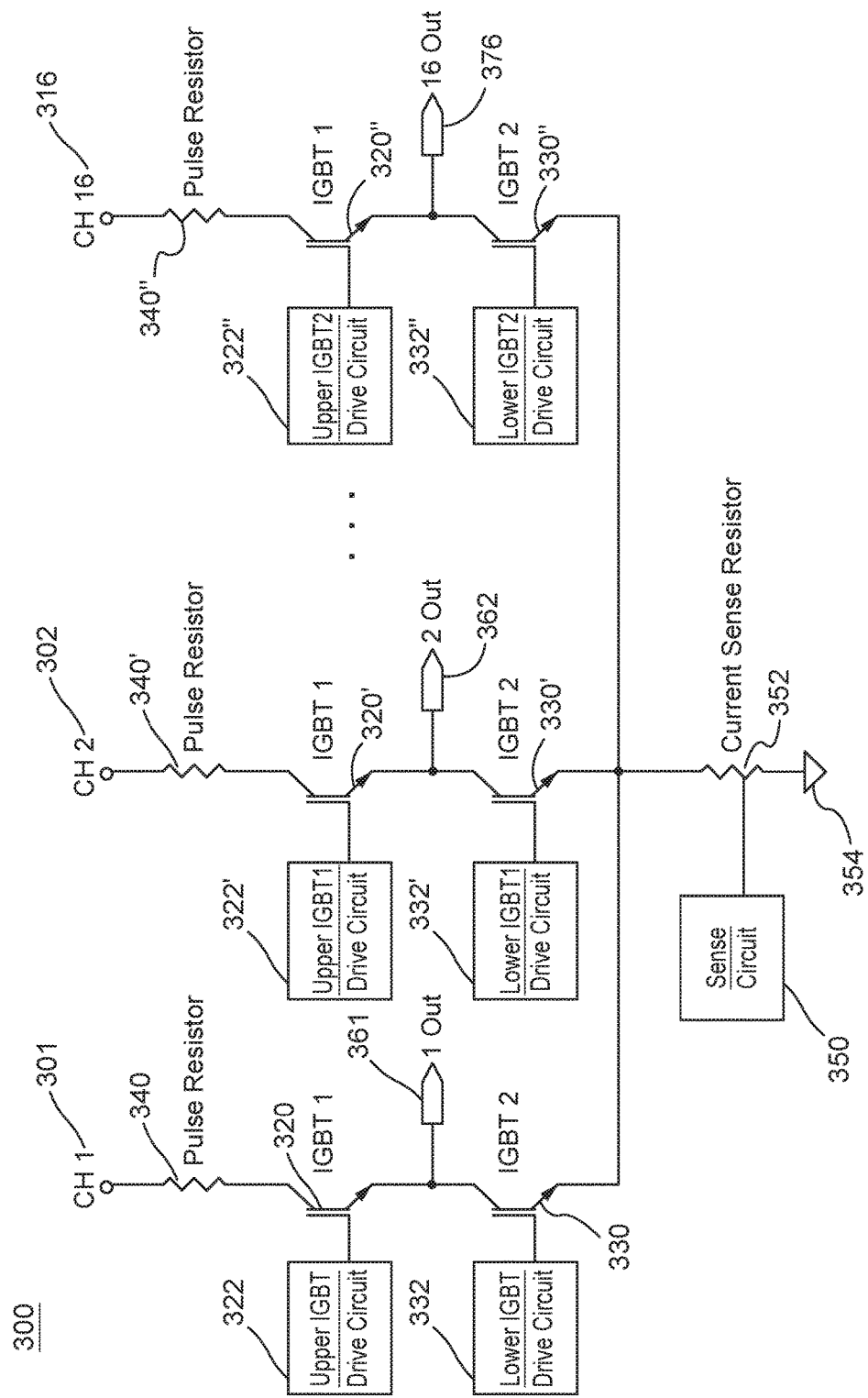
FIG. 3 is a circuit diagram of a signal generator, according to other embodiments.

FIG. 3 illustrates a circuit diagram of an embodiment of a signal generator (300) that may be structurally and/or functionally similar to signal generator (110). For example, the signal generator (300) may include one or more electrode channels (301, 302, 316) that may be structurally and/or functionally similar to the electrode channels (124a, 124b, . . . , 124n). For ease of explanation, unless explicitly noted otherwise, elements in FIG. 3 may have the same components, functionality, and/or values as discussed with respect to similar elements in FIG. 2. For example, the electrode channels (201, 202, 203) used to deliver pulse waveforms to a set of electrodes in FIG. 2 may be the same set of electrode channels (301, 302, 316) used for capacitive energy discharge in FIG. 3. The signal generator (300) may include one or more electrode channels (301, 302, . . . , 316) where FIG. 3 illustrates each of the electrode channels having a same circuit configuration. FIG. 3 illustrates 16 electrode channels, although it should be appreciated that the signal generator (300) may include N number of electrode channels, for example, 1, 2, 3, 4, 5, 6, 7, 8, 9, 10, 12, 14, 16, 18, 20, or more electrode channels. A first electrode channel (301) may include a first electronic switch (320) configured to switch between an ON state and an OFF state. A first drive circuit (322) may be coupled to the gate terminal of the first electronic switch (320) to control the state of the first electronic switch (320). The first electrode channel (301) may further include a second electronic switch (330) configured to switch between an ON and an OFF state. A second drive circuit (332) may be coupled to the gate terminal of the second electronic switch (330) to control the state of the second electronic switch (330). An output channel (361) may be coupled between the emitter terminal of the first electronic switch (320) and the collector terminal of the second electronic switch (330).

Likewise, a second and sixteenth electrode channel (302, 316) may include respective first electronic switches (320', 320") configured to switch between an ON state and an OFF state. The first drive circuits (322', 322") may be coupled to respective first electronic switches (320', 320") to control the state of the first electronic switches (320', 320"). Output channels (362, 376) may be coupled between the emitter terminal of the first electronic switches (320', 320") and the collector terminal of the second electronic switches (330', 330"). The second and sixteenth electrode channels (302, 316) further include respective second electronic switches (330', 330") configured to switch between an ON and an OFF state. A second drive circuit (332', 332") may be coupled to the gate terminal of the second electronic switch (330', 330") to control the state of the second electronic switch (330', 330"). Each of the output channels (361, 362, 376) may be coupled to respective electrodes on one or more medical devices (not shown). Each electrode channel (301, 302, 316) may thus correspond to a respective electrode of the set of electrodes on one or more medical devices.

The electronic switches as described herein may include one or more bipolar transistors. In some embodiments, one or more of the electronic switches include insulated-gate bipolar transistors. An energy source (not shown) may be coupled to the collector terminals of the first electronic switches (320, 320', 320") of the electrode channel (301, 302, 316) through respective resistive elements (340, 340', 340"). The resistive elements (340, 340', 340") may each be configured to discharge a capacitive element of the energy source when the energy source is not in use. Each of the electrode channels (301, 302, 316) may be coupled to a sensing circuit (350) and current sense resistor (352). In some embodiments, the sensing circuit (350) may be configured to detect arcing during use. In FIG. 3, the sensing circuit (350) may be coupled between the emitter terminal of the second electronic switches (330, 330', 330") and ground (354). Additionally or alternatively, each electrode channel (301, 302, 316) may be coupled to a respective sensing circuit (350) and current sense resistor (352).

In some embodiments, as described with respect to FIGS. 1 and 3, the signal generator (110) may provide active monitoring of the electrode channels. For example, the processor (120) of the signal generator (110) may be configured to perform one or more fault tests to verify operation of one or more electrode channels (124a, 124b, . . . , 124n) (e.g., electronic switches and drive circuits), the energy source (126) (e.g., DC power supply), and sensing circuit (128) (e.g., arc detection). The fault tests may be performed on one or more electrode channels (124a, 124b, . . . , 124n) at predetermined intervals (e.g., upon startup before delivery of a pulse waveform, between delivery of pulse waveforms, when the energy source (126) is not in use). In some embodiments, the signal generator (300) may perform a series of fault tests on one or more electrode channels to classify a working state of one or more electrode channels. In one embodiment, after delivery of a pulse waveform to a set of electrodes (142a, 142b, . . . , 142n) at a first time, a first fault test may be conducted individually for one or more of the set of electrode channels (301, 302, . . . , 316). In some embodiments, the first fault test may include, for the first electrode channel (301), setting the first electronic switch (320) to the ON state and the second electronic switch (330) to the OFF state. A verification DC voltage may be applied to the first electrode channel (301) for fault testing. In one embodiment, the verification DC voltage may be about 50V. The first electrode channel (301) may be classified as passing the first fault test when substantially no current is detected by the sensing circuit (350) during the first fault test. The first electrode channel (301) may be classified as failing the first fault test (e.g., in fault) when a threshold current, for example a current of 10 mA or higher, is detected by the sensing circuit (350). In some embodiments, the second fault test may include, for the first electrode channel (301), setting the first electronic switch (320) to the OFF state and the second electronic switch (330) to the ON state. The first electrode channel (301) may be classified as passing the second fault test when substantially no current is detected by the sensing circuit (350) during the second fault test. The first electrode channel (301) may be classified as failing the second fault test when a threshold current, for example a current of 10 mA or higher, is detected by the sensing circuit (350). In some embodiments, the third fault test may include, for the first electrode channel (301), setting the first electronic switch (320) to the ON state and the second electronic switch (330) to the ON state. The first electrode channel (301) may be classified as passing the third fault test when a predetermined amount of current is detected by the sensing circuit (350) during the third fault test and classified as failing the third fault test when the sensing circuit (350) detects a non-predetermined amount of current. For example, the predetermined amount of current (e.g., about 5 A) may be equal to a DC voltage output by the energy source (e.g., about 50 V) divided by a resistance of the resistive element (340) (e.g., about 10Ω).

A failure in the first fault test may indicate a malfunction in the second electronic switch (330) and/or second drive circuit drive (332) (e.g., lower IGBT circuitry in FIG. 3) while a failure in the second fault test may indicate a malfunction in the first electronic switch (320) and/or first drive circuit (322) (e.g., upper IGBT circuitry in FIG. 3). A failure in the third fault test may indicate a malfunction in one or more of the energy source, sensing circuit, electronic switches, and drive logic. Accordingly, the fault tests may verify the individual and collective operation of upper and lower IGBT circuitry for a fault tested electrode channel. Each of the fault tests described herein may be performed for each electrode channel (301, 302, . . . , 316) at a predetermined interval.

In some embodiments, a fault test may be performed for an electrode channel (124) based on predetermined criteria (e.g., a predetermined number of pulses delivered, a predetermined amount of energy delivered, and/or the like). Each electrode channel or a subset of electrode channels may be verified. For example, fault tests may be performed on each electrode channel (124) configured as an anode, or for each electrode channel (124) after delivery of 5 pulses. In some embodiments, the fault tests may be conducted in conjunction with voltage pulse waveform delivery and capacitor discharge, as described in more detail herein.

The generation and delivery of high voltage pulse waveforms using a signal generator as described herein may lead to an energy source (e.g., one or more capacitors) of the signal generator storing excess energy. This energy may be discharged to ground through a set of discharge pulses using the electrode channels. Discharge may be performed prior to delivering subsequent pulse waveforms. In other words, the electrode channels may be used to deliver tissue ablation energy to one or more electrodes as well as discharge excess energy to ground. This configuration may be used in place of a dump circuit and/or bleeder resistor circuit for discharging excess stored energy in the signal generator.

In some embodiments, as described with respect to FIGS. 1 and 3, each electrode channel (124) may sequentially partially discharge the energy source (126) to ground over a set of cycles. Each electrode channel (124) may be configured as a half bridge amplifier to partially discharge the energy source to ground. The energy source (126) may complete discharge of a predetermined amount of energy within seconds. As used herein, a discharge cycle refers to energy discharge of the energy source to ground using each of the electrode channels of the set of electrode channels. For example, energy may be partially discharged to ground one at a time through each electrode channel (124) of a signal generator (110). In some embodiments, fault detection may be performed on the electrode channels (124) at pre-determined intervals (e.g., before each discharge cycle, after a predetermined number of discharge cycles, etc.) to ensure that energy discharge is performed as intended. As stored energy is reduced through discharging, a pulse width of a discharge pulse may be increased without causing damage to the electrode channels (124). For example, an initial, first amount of stored energy (e.g., about 3 kJ) of the energy source (126) may correspond to discharge pulses having a first predetermined pulse width (e.g., about 0.5 µs). After discharge of the energy source to a second amount of stored energy, the pulse width of the discharge pulses may be configured to a second predetermined pulse width (e.g., about 2 µs).

In some embodiments, the set of electrode channels illustrated in FIG. 3 may correspond to a set of discharge paths to ground to reduce an amount of stored energy of an energy source (126). In some embodiments, the first electrode channel (301) of the set of electrode channels (301, 302, . . . , 316) may be configured to partially discharge energy to ground after a delivering a pulse waveform to a set of electrodes (142). For example, the first electronic switch (320) may be set to the ON state and the second electronic switch (330) may be set to the ON state for a predetermined duration of time to at least partially discharge the energy source (126). This current through the first electrode channel (301) may be about equivalent to the DC voltage of the energy source (126) divided by a resistance of the resistive element (340). The first electrode channel (301) may discharge energy to ground using a predetermined pulse width (e.g., about 0.5 µs).

Once the first electrode channel (301) partially discharges the energy source (126), each of the remaining electrode channels (302, . . . , 316) may be configured to partially discharge the energy source (126) one at a time in a manner analogous to the first electrode channel (301). In some embodiments, a channel inactive time period (e.g., dead time) may follow the partial energy discharge of an electrode channel. For example, a channel inactive time period following each electrode channel energy discharge may be about 100 µs. In some embodiments, a discharge cycle inactive time period may follow each discharge cycle. For example, a discharge cycle inactive time period may be about 5 ms and may correspond to a bootstrap charge time. By staggering the discharge of each electrode channel, the signal generator (300) may discharge capacitor energy at a faster rate than conventional circuit topologies.

The set of electrode channels (124) may discharge the energy source to ground sequentially over a set of discharge cycles until reaching a predetermined energy threshold. In some embodiments, energy discharge may be performed such that a pulse width increases over time or over each discharge cycle. The number of pulses may decrease as the pulse width increases. In some embodiments, energy discharge may be configured as follows: a first pulse width may be between about 0.1 µs and about 1 µs and may be set between about 90 discharge cycles and about 130 discharge cycles; a second pulse width may be between about 1 µs and about 5 µs and may be set between about 80 discharge cycles and about 90 discharge cycles; a third pulse width may be between about 5 µs and about 10 µs and may be set between about 70 discharge cycles and about 80 discharge cycles; a fourth pulse width may be between about 10 µs and about 15 µs and may be set for about 70 discharge cycles or less; and a fifth pulse width may be between about 15 µs and about 25 µs and may be set for about 70 discharge cycles or less.

In one merely illustrative and non-limiting example, a set of 16 electrode channels may be used to discharge to ground an energy source of about 3 kJ at an average rate of about 1 kJ/sec such that the signal generator may complete discharge in about 3 seconds. In one embodiment, energy discharge may be configured as follows: a first pulse width of about 0.5 µs may be set for about 110 discharge cycles over about 730 ms; a second pulse width of about 2 µs may be set for about 80 discharge cycles over about 530 ms; a third pulse width of about 6 µs may be set for about 73 discharge cycles over about 490 ms; a fourth pulse width of about 12.5 µs may be set for about 70 discharge cycles over about 480 ms; and a fifth pulse width of about 25 µs may be set over about 780 ms for any remaining discharge cycles left to complete the energy source discharge.

In some embodiments, fault detection as described herein may be performed on an electrode channel prior to a partial energy discharge using that electrode channel. If the electrode channel is determined to be in a fault state, the electrode channel may be excluded from the set of electrode channels used to discharge the energy source to ground and/or the fault status may be output to the operator. Verification of the electrode channels may be performed for each of the electrode channels or a subset of the electrode channels at predetermined intervals such as for: each energy discharge pulse; one or more discharge cycles (e.g., fault test the electrode channels after each cycle or every other cycle); pulse width transitions (e.g., fault detect the electrode channels between every increase in pulse width); and a predetermined time interval (e.g., fault test the electrode channels every 0.1 seconds, 0.25 seconds, 0.5 seconds, 1 second, etc.).

Ablation Device

Figure 4A:
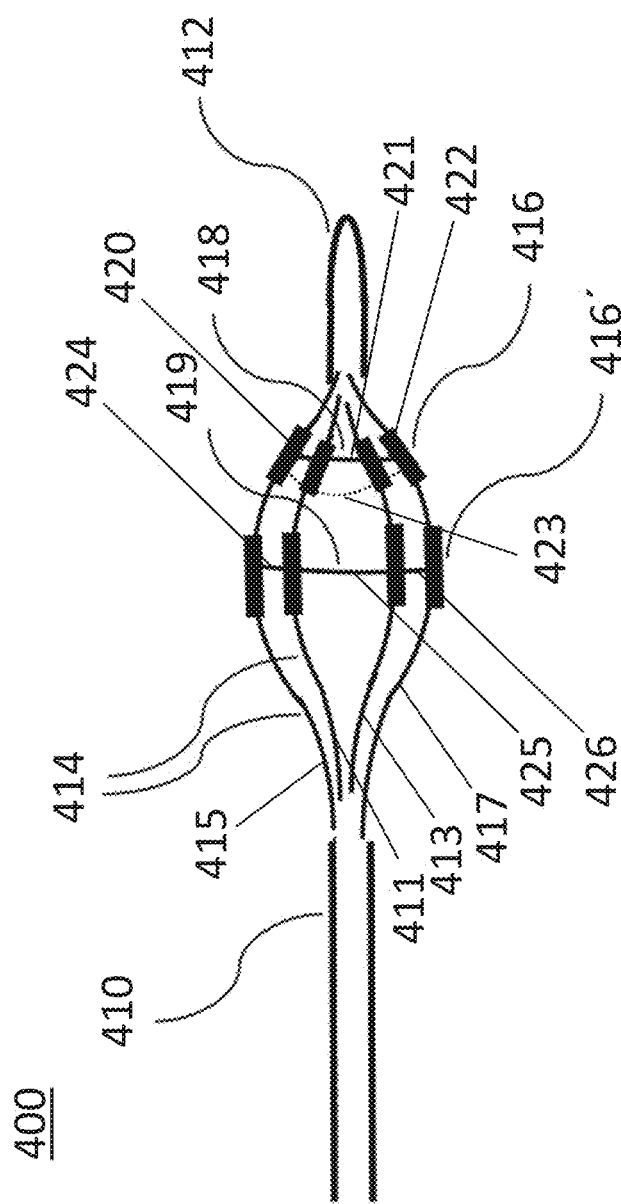
FIG. 4A is a side view of an ablation catheter, according to other embodiments.

The systems described here may include one or more multi-electrode ablation devices configured to ablate heart tissue for treating atrial fibrillation such as in a left atrial chamber of a heart. FIG. 4A illustrates an embodiment of an ablation device (e.g., structurally and/or functionally similar to the ablation device (140)) that may be configured to deliver voltage pulse waveforms using a set of electrodes to ablate tissue and electrically isolate a pulmonary vein. In some of these embodiments, the ablation device may be transformed from a first configuration to a second configuration such that the electrodes of the ablation device expand outward to contact a lumen or an ostium or an antrum of an orifice in tissue (e.g., pulmonary vein ostium or pulmonary vein antrum).

The ablation device (400) includes a catheter shaft (410) at a proximal end of the device (400), a distal cap (412) of the device (400), and a set of splines (414) coupled thereto. The distal cap (412) may include an atraumatic shape. A proximal end of the set of splines (414) may be coupled to a distal end of the catheter shaft (410), and a distal end of the set of splines (414) may be tethered to the distal cap (412) of the device (400). Each spline (414) of the ablation device (400) may include one or more independently addressable electrodes (416) formed on a surface of the spline (414). Each electrode (416) may include an insulated electrical lead configured to sustain a voltage potential of at least about 700 V without dielectric breakdown of its corresponding insulation. In other embodiments, the insulation on each of the electrical leads may sustain an electrical potential difference of between about 200V to about 1500 V across its thickness without dielectric breakdown. Each spline (414) may include the insulated electrical leads of each electrode (416) formed in a body of the spline (414) (e.g., within a lumen of the spline (414)). A set of spline wires (418, 419) may be electrically conductive and electrically couple adjacent electrodes (416) disposed on different splines (414). For example, the spline wire (418) (connecting electrodes (416)) and the spline wire (419) (connecting electrodes (416')) may extend in a transverse direction relative to a longitudinal axis of the ablation device (400).

FIG. 4A illustrates a set of splines (414) where each spline (414) includes a pair of electrodes (416 and 416') having about the same size, shape, and spacing as the electrodes (416 and 416') of an adjacent spline (414). In other embodiments, the size, shape, and spacing of the electrodes (416, 416') may differ. For example, the electrodes (416) electrically coupled to a first spline wire (418) may differ in size and/or shape from electrodes (416') electrically coupled to a second spline wire (419).

In some embodiments, the first spline wire (418) may include a first set of spline wires (420, 421, 422, 423), where each spline wire of the set of spline wires (420, 421, 422, 423) may couple electrodes (416) between a different pair of splines of the set of splines (414). In some of these embodiments, the set of spline wires (420, 421, 422, 423) may form a continuous loop between the electrodes (416) coupled thereto. Likewise, the second spline wire (419) may include a second set of spline wires (424, 425, 426), where each spline wire of the set of spline wires (424, 425, 426) may couple electrodes (416') across the set of splines (414). The second set of spline wires (424, 425, 426) may couple different electrodes (416') across the set of splines (414) than the first set of spline wires (420, 421, 422, 423). In some of these embodiments, the first set of spline wires (420, 421, 422, 423) may form a first continuous loop between the electrodes (416) coupled thereto and the second set of spline wires (424, 425, 426) may form a second continuous loop between the electrodes (416') coupled thereto. The first continuous loop may be electrically isolated from the second continuous loop. In some of these embodiments, the electrodes (416) coupled to the first continuous loop may be configured as anodes and the electrodes (416') coupled to the second continuous loop may be configured as cathodes. A pulse waveform generated by a signal generator may be delivered to the electrodes (416 and 416') of the first and second continuous loop. In some embodiments, the spline wires such as 421, 422, 423, etc. may be replaced by similar electrical connections in the proximal part of the device (for example, in the device handle). For example, the electrodes (416) may all be electrically wired together in the handle of the device.

Figure 4B:
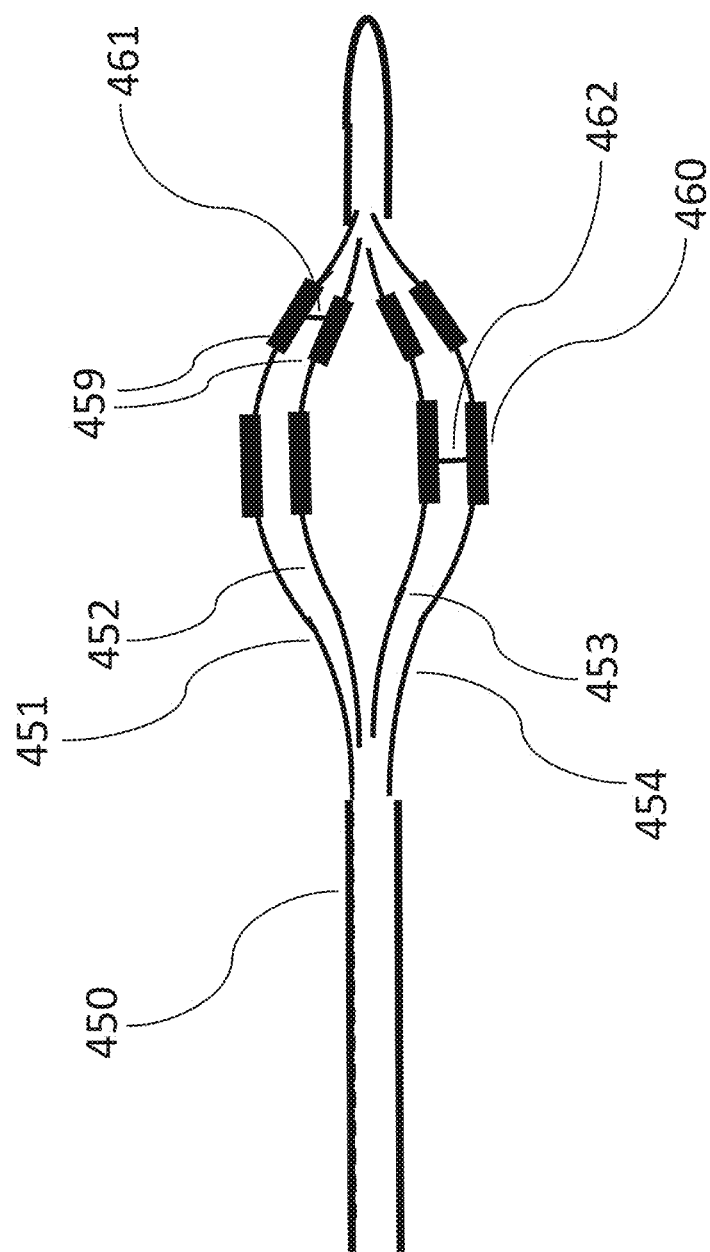
FIG. 4B is a side view of an ablation catheter, according to other embodiments.

In another embodiment illustrated in FIG. 4B, the first spline wire (461) of the set of spline wires (461, 462) may couple electrodes (459) between a first spline (451) and a second spline (452) of the set of splines, and a second spline wire (462) of the set of spline wires (461, 462) may couple electrodes (460) between the third spline (453) and a fourth spline (454) of the set of splines. The electrodes (459) coupled by the first spline wire (461) and the electrodes (460) coupled by the second spline wire (462) may be configured as an anode and cathode respectively (or vice-versa). A pulse waveform may be delivered to the electrodes (459) coupled by the first spline wire (461) and the electrodes (460) coupled by the second spline wire (462). In some embodiments, instead of spline wires the electrical leads of at least two electrodes of the set of electrodes may be electrically coupled at or near a proximal portion of the ablation device, such as, for example, within a handle.

In other embodiments, referring to FIG. 4A, one or more of the spline wires (418, 419) may form a continuous loop between the electrically coupled electrodes (416). For example, a first set of spline wires (418) may form a first continuous loop between the electrodes (416) coupled thereto and a second set of spline wires (419) may form a second continuous loop between the electrodes (416') coupled thereto. In this case, the first continuous loop may be electrically isolated from the second continuous loop. In one embodiment, each of the electrodes (416) coupled to a first set of spline wires (418) may be configured as an anode while each of the electrodes (416) coupled to a second set of spline wires (419) may be configured as a cathode. Each group of electrically coupled electrodes (416) may be independently addressable. In some embodiments, instead of spline wires the electrical leads of at least two electrodes of the set of electrodes may be electrically coupled at or near a proximal portion of the ablation device, such as, for example, within a handle.

In other embodiments, the size, shape, and spacing of the electrodes (416) may differ. The ablation device (400) may include any number of splines, for example, 3, 4, 5, 6, 7, 8, 9, 10, 12, 14, 16, 18, 20, or more splines. In some embodiments, the ablation device (400) may include 3 to 20 splines. For example, in one embodiment, the ablation device (400) may include between 4 and 9 splines.

For each of the ablation devices described herein, each of the splines may include a polymer and define a lumen so as to form a hollow tube. The one or more electrodes of the ablation device described herein may include a diameter from about 0.2 mm to about 2.5 mm and a length from about 0.2 mm to about 5.0 mm. In some embodiments, the electrode may include a diameter of about 1 mm and a length of about 1 mm. As the electrodes may be independently addressable, the electrodes may be energized in any sequence using any pulse waveform sufficient to ablate tissue by irreversible electroporation. For example, different sets of electrodes may deliver different sets of pulses (e.g., hierarchical pulse waveforms). It should be appreciated that the size, shape, and spacing of the electrodes on and between the splines may be configured to deliver energy sufficient to generate contiguous/transmural lesions in order to electrically isolate one or more pulmonary veins. In some embodiments, alternate electrodes (e.g., all the distal electrodes) may be at the same electric potential, and likewise for all the other electrodes (e.g., all the proximal electrodes). Thus, ablation may be delivered rapidly with all electrodes activated at the same time. A variety of such electrode pairing options exist and may be implemented based on the convenience thereof.

For each of the ablation devices discussed herein, the electrodes (e.g., ablation electrode, return electrode) may include biocompatible metals such as titanium, palladium, silver, platinum or a platinum alloy. For example, the electrode may preferably include platinum or a platinum alloy. Each electrode may include an electrical lead having sufficient electrical insulation to sustain an electrical potential difference of at least 700V across its thickness without dielectric breakdown. In other embodiments, the insulation on each of the electrical leads may sustain an electrical potential difference of between about 200 V to about 2500 V across its thickness without dielectric breakdown, including all values and sub-ranges in between. The insulated electrical leads may run to the proximal handle portion of the catheter from where they may be connected to a suitable electrical connector. The catheter shaft may be made of a flexible polymeric material such as Teflon, Nylon, Pebax, etc.

FIG. 5 illustrates an embodiment of an ablation device (500) (e.g., structurally and/or functionally similar to the ablation device (140)) that may be configured to deliver voltage pulse waveforms generated by a signal generator (110) as described herein using a set of electrodes to ablate tissue which in some embodiments may generate a linear circumferential ablation lesion. The ablation device (500) may include a catheter (510) having a flexible elongate shaft (520). The elongate shaft (520) may be advanced and withdrawn from a lumen of the catheter (510). The flexibility of the catheter (510) may facilitate positioning of the electrodes (530) around asymmetric and/or complex contours. The elongate shaft (520) may include a set of electrodes (530) spaced apart along the elongate shaft (520). In some embodiments, the electrodes (530) may be integrally formed with the elongate shaft (520). Each of the electrodes (530) may be connected to a respective output channel of a signal generator. The electrodes (530) may be independently configured as an anode or cathode and configured to deliver a pulse waveform to target tissue to perform ablation. In some embodiments, the set of electrodes (530) may have a spacing (532) between electrodes configured to create a contiguous ablation lesion such as a circumscribing lesion around a left atrial target and pulmonary vein. In some embodiments, the ratio of the spacing (532) between consecutive electrodes (530) to the longitudinal length of each electrode may be less than about 3:1, and may be less than about 2:1.

II. Methods

Also described here are methods for delivering pulse waveform using the systems and devices described herein. Generally, the methods described here include configuring a set of electrode channels and output channels to deliver a voltage pulse waveform to one or more electrodes of an ablation device for tissue ablation. Some embodiments of the methods also describe signal generator fault monitoring and high energy discharge of an energy source (e.g., capacitor dump). These methods may allow arbitrary electrode selection, provide fault detection, and improve operation speed for therapeutic procedures including atrial fibrillation. Additionally or alternatively, the pulse waveforms may include a set of levels of a hierarchy to reduce total energy delivery. Additionally or alternatively, a cardiac pacing signal may synchronize the delivered pulse waveforms with the cardiac cycle. The tissue ablation thus performed may be delivered in synchrony with paced heartbeats and with less energy delivery to reduce damage to healthy tissue. It should be appreciated that any of the ablation devices described herein may be used to ablate tissue using the methods discussed below as appropriate. For example, the methods disclosed herein are usable with any of the systems (100, 200, 300) and ablation devices (e.g., 140, 400, 500) described herein.

Figure 6:
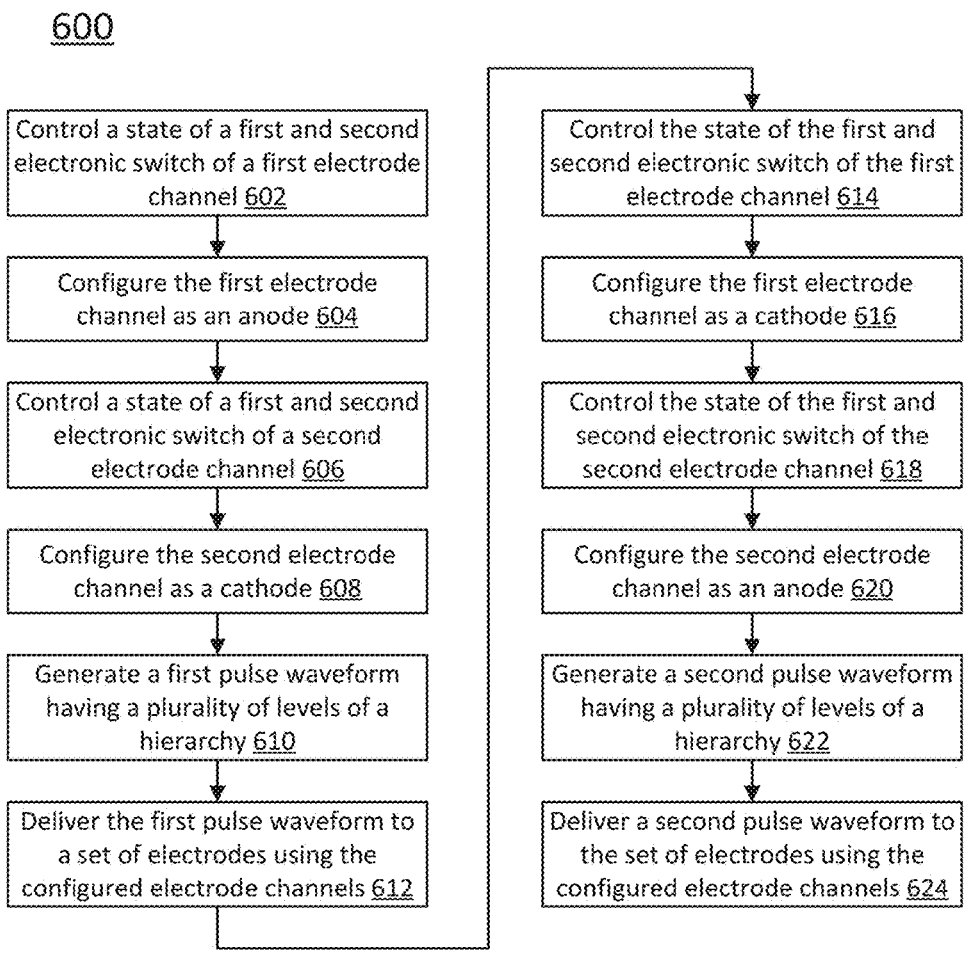
FIG. 6 illustrates a method for tissue ablation, according to embodiments.

FIG. 6 is a method (600) for one embodiment of a signal generation process using the systems and devices described herein. The method (600) includes controlling a state of a first and second electronic switch of a first electrode channel (602). For example, step 602 may control a state of first electronic switch (220) and second electronic switch (230) of the first electrode channel (201) illustrated in FIG. 2. In some embodiments, a drive circuit (e.g., drive circuits (222, 232)) coupled to an electronic switch may be configured to control the state of the electronic switch. In some embodiments, the electronic switch may be configured to switch between an ON state and an OFF state using the drive circuit. The first electrode channel may be configured as an anode (604). A state of a first and second electronic switch of a second electrode channel may be controlled (606) by, for example, drive circuits controlling the ON/OFF states of respective electronic switches. The second electrode channel may be configured as a cathode (608).

In some embodiments, hierarchical voltage pulse waveforms having a nested structure and a hierarchy of time intervals, as described herein, may be useful for irreversible electroporation, as well as providing control and selectivity in different tissue types. In some embodiments, a first pulse waveform may be generated having a set of levels of a hierarchy (610). In some embodiments, a first level of a hierarchy of the first pulse waveform may include a first set of pulses, with each pulse having a pulse time duration. A first time interval may separate successive pulses. A second level of the hierarchy of the first pulse waveform may include a set of first sets of pulses as a second set of pulses with a second time interval separating successive first sets of pulses. The second time interval may be at least three times the duration of the first time interval. A third level of the hierarchy of the pulse waveform may include a set of second sets of pulses as a third set of pulses with a third time interval separating successive second sets of pulses. The third time interval may be at least thirty times the duration of the second level time interval. An energy source may deliver the first pulse waveform to a set of electrodes during use via the first electrode channel and the second electrode channel (612). The first pulse waveform may be delivered at a first time.

At a second time subsequent to the first time, the state of the first and second electronic switch of the first electrode channel may be controlled (614). The first electrode channel may be configured as a cathode (616). The state of the first and second electronic switch of the second electrode channel may be controlled (618). The second electrode channel may be configured as an anode (620). In some embodiments, a second pulse waveform may be generated having a set of levels of a hierarchy (622), such as including the first, second, and third hierarchy levels described herein. The energy source may deliver the second pulse waveform to the set of electrodes during use via the first electrode channel and the second electrode channel at the second time (624).

Fault Detection

Figure 7A:
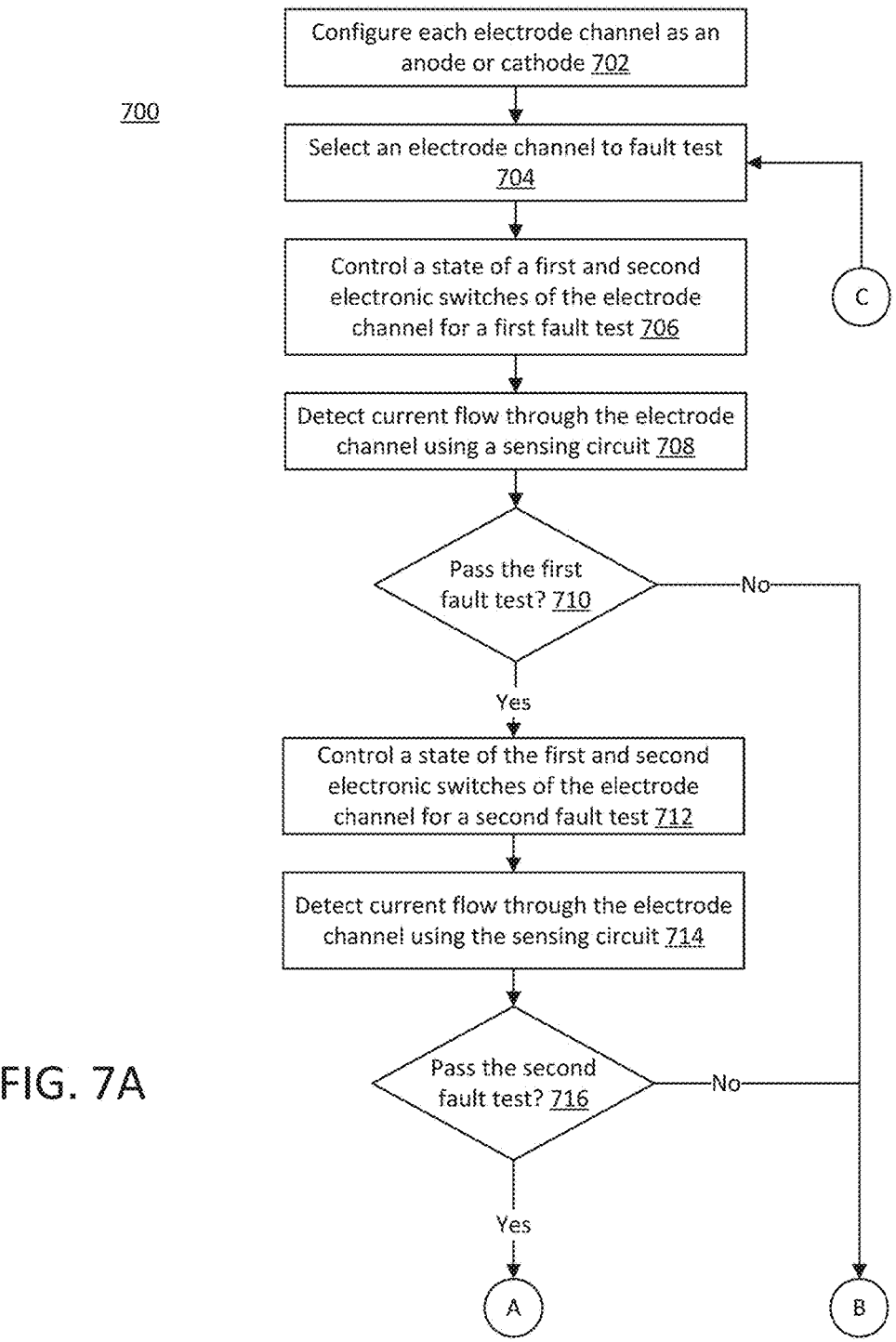
FIGS. 7A-7B illustrate a method for fault detection, according to other embodiments.
Figure 7B:
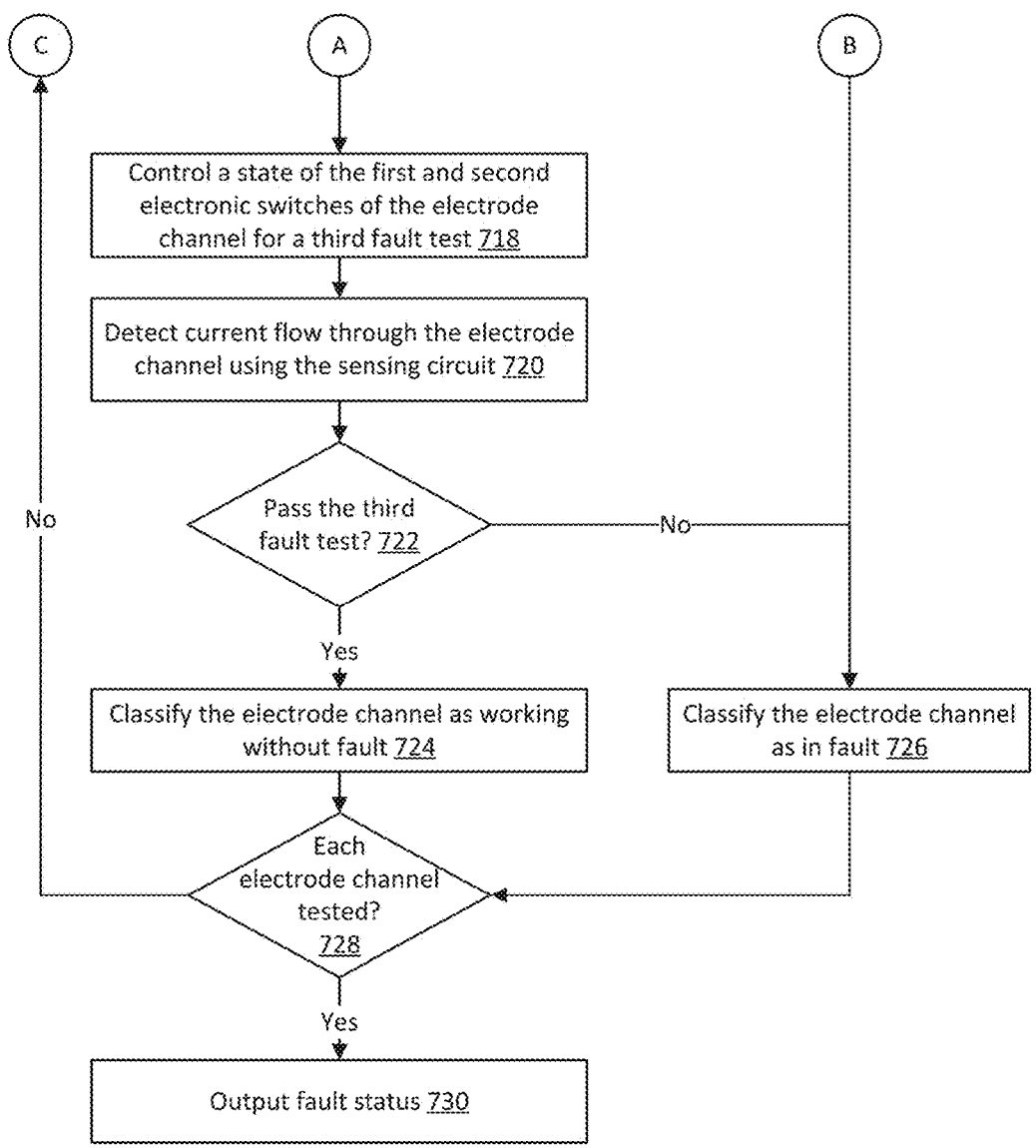

FIGS. 7A-7B illustrate a method (700) for one embodiment of a fault detection process using the systems and devices described herein. The methods disclosed herein are usable with any of the systems (100, 200, 300) and ablation devices (e.g., 140, 400, 500) described herein. The method (700) may optionally include configuring each electrode channel as an anode or cathode (702), such as described in FIG. 6. An electrode channel may be selected to fault test based on predetermined criteria as described herein. For example, an electrode channel may be selected for fault testing based on a number of pulses delivered by the electrode channel, an amount of energy delivered by the electrode channel, and/or the like. Furthermore, one or more electrode channels may be selected for fault testing upon powering on a signal generator and/or before delivery of a pulse waveform. Each electrode channel or a subset of electrode channels may be selected one at a time for fault testing. For example, fault tests may be performed on each electrode channel configured as an anode or each electrode channel configured as a cathode.

A state of a first and second electronic switch of the selected electrode channel may be controlled to perform a first fault test (706). For example, a first electronic switch may be set to the ON state and a second electronic switch may be set to the OFF state. Current through the selected electrode channel may be detected using a sensing circuit (708). The selected electrode channel may be classified by a processor (e.g., processor (120)) as passing the first fault test (710—Yes) when substantially no current is detected by the sensing circuit. A state of a first and second electronic switch of the selected electrode channel may be controlled to perform a second fault test (712). For example, a first electronic switch may be set to the OFF state and a second electronic switch may be set to the ON state. Current through the selected electrode channel may be detected using the sensing circuit (714). The selected electrode channel may be classified by the processor as passing the second fault test (716—Yes) when substantially no current is detected by the sensing circuit. A state of a first and second electronic switch of the selected electrode channel may be controlled to perform a third fault test (718). For example, a first electronic switch may be set to the ON state and a second electronic switch may be set to the ON state. Current through the selected electrode channel may be detected using the sensing circuit (720). The selected electrode channel may be classified by the processor as passing the third fault test (722—Yes) when a predetermined amount of current is detected by the sensing circuit. For example, the predetermined amount of current may be equal to about a DC voltage output by the energy source divided by a resistance of a resistive element. The selected electrode channel passing each of the first, second, and third fault tests may be classified by the processor as working without fault (724). However, when the selected electrode channel fails to pass any of the first, second, and third fault tests (710—No, 716—No, 722—No), the selected electrode channel may be classified by the processor as in fault (726). A determination by the processor may be performed of whether each electrode channel has been fault tested (728), and the process may return to step 704 when another electrode channel is to be fault tested (728—No). Upon completing fault testing of each electrode channel to be tested (728—Yes), a fault status may be output (730).

Energy Discharge

Figure 8:
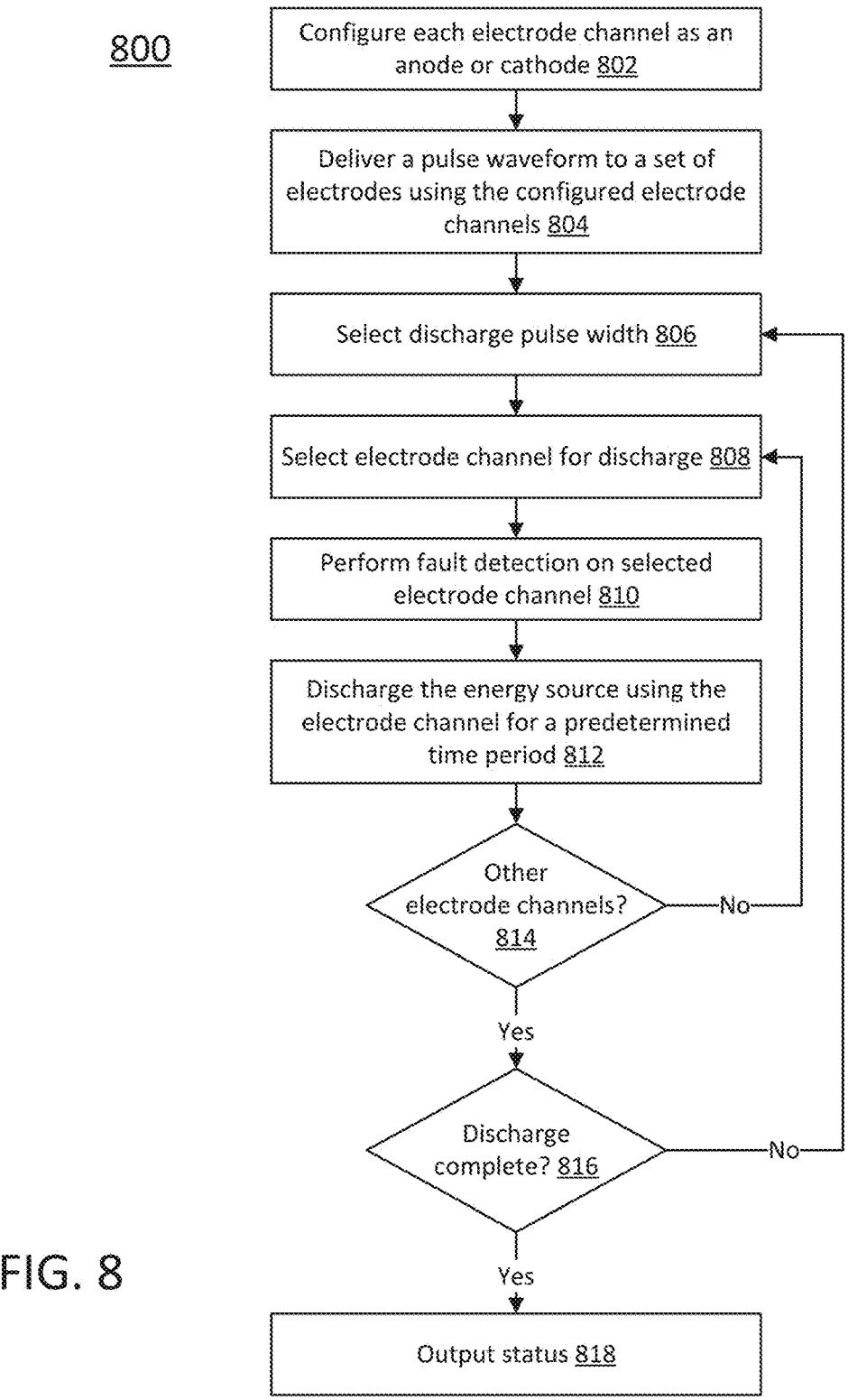
FIG. 8 illustrates a method for energy discharge, according to other embodiments.

FIG. 8 is a method (800) for one embodiment of an energy discharge process using the systems and devices described herein. The methods disclosed herein are usable with any of the systems (100, 200, 300) and ablation devices (e.g., 140, 400, 500) described herein. The method (800) may optionally include configuring each electrode channel as an anode or cathode (802) and delivering a pulse waveform using an energy source to a set of electrodes using the configured electrode channels (804). A discharge pulse width may be selected (806). In some embodiments, a discharge pulse width may be selected by a processor (e.g., processor (120)) based on an amount of energy stored in the energy source to be discharged to ground. For example, a higher amount of stored energy in the energy source may correspond to a narrower pulse width. In some embodiments, energy discharge may be performed upon completion of a treatment procedure (e.g., tissue ablation) and/or upon powering off of a signal generator (110). As energy is discharged to ground over a set of discharge cycles, the pulse width may be increased at predetermined intervals, such as those described herein. An electrode channel may be selected by the processor for discharge (808). Fault detection, as discussed with respect to FIGS. 7A-7B and as described herein, may optionally be performed on the selected electrode channel (810). When the selected electrode channel passes fault testing, the energy source may be discharged using the electrode channel for a predetermined time period (812). A determination by the processor may be performed of whether other electrode channels in the set of electrode channels have completed energy discharge (814). For example, a determination may be performed of whether a discharge cycle (e.g., discharge by each electrode channel in the set of electrodes) has been completed. The method may return to step 808 when one or more electrode channels remain in a discharge cycle (814—No). The method may proceed to step 816 when a discharge cycle has been completed (814—Yes). A determination by the processor may be performed of whether the energy source has completed discharge (816). For example, a set of discharge cycles may be performed using the electrode channels until the energy source reaches a predetermined energy threshold. The method may return to step 806 when energy source discharge has not been completed (816—No). A status may be output (818) when energy source discharge has been completed (816—Yes).

Pulse Waveform

Disclosed herein are methods, systems and devices for the selective and rapid application of pulsed electric fields/waveforms to effect tissue ablation with irreversible electroporation. The pulse waveform(s) as disclosed herein are usable with any of the systems (100, 200, 300), ablation devices (e.g., 140, 400, 500), and methods (e.g., 600, 700, 800) described herein. Some embodiments are directed to pulsed high voltage waveforms together with a sequenced delivery scheme for delivering energy to tissue via sets of electrodes. In some embodiments, peak electric field values may be reduced and/or minimized while at the same time sufficiently large electric field magnitudes may be maintained in regions where tissue ablation is desired. This also reduces the likelihood of excessive tissue damage or the generation of electrical arcing, and locally high temperature increases. In some embodiments, a system useful for irreversible electroporation may include a signal generator capable of being configured to deliver pulsed voltage waveforms to a set of electrodes of an ablation device. In some embodiments, a processor of the signal generator is configured to control a set of electrode channels whereby selected pairs of anode-cathode subsets of electrodes may be sequentially triggered based on a pre-determined sequence, and in one embodiment the sequenced delivery may be triggered from a cardiac stimulator and/or pacing device. In some embodiments, the ablation pulse waveforms may be applied in a refractory period of the cardiac cycle so as to avoid disruption of the sinus rhythm of the heart. One example method of enforcing this is to electrically pace the heart with a cardiac stimulator (e.g., cardiac stimulator (150)) and ensure pacing capture to establish periodicity and predictability of the cardiac cycle, and then to define a time window well within the refractory period of this periodic cycle within which the ablation waveform is delivered.

In some embodiments, the pulsed voltage waveforms disclosed herein are hierarchical in organization and have a nested structure. In some embodiments, the pulsed waveform includes hierarchical groupings of pulses with a variety of associated timescales. Pulsed waveforms for electroporation energy delivery as disclosed herein may enhance the safety, efficiency and effectiveness of the energy delivery by reducing the electric field threshold associated with irreversible electroporation, yielding more effective ablative lesions with reduced total energy delivered. This in turn may broaden the areas of clinical application of electroporation including therapeutic treatment of a variety of cardiac arrhythmias.

Figure 9:
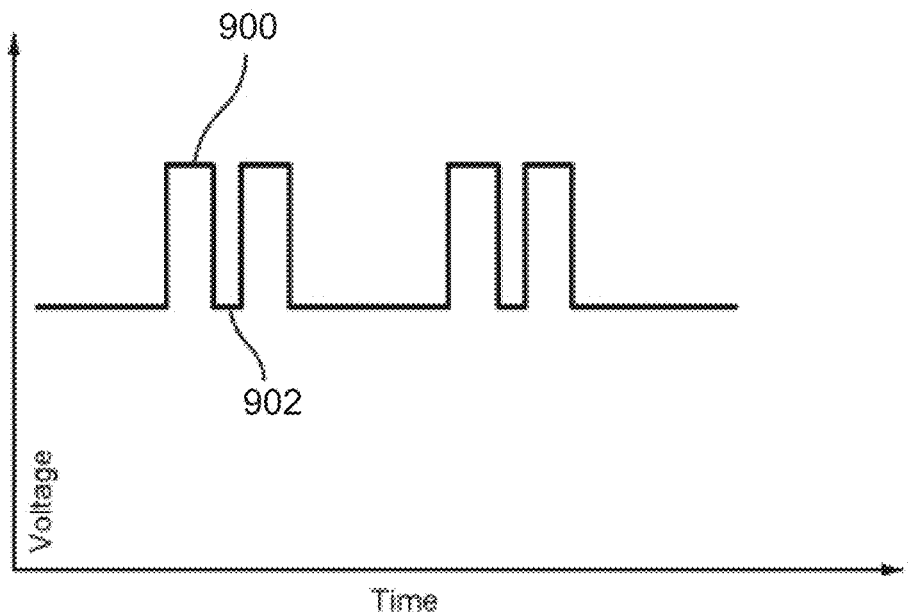
FIG. 9 is an example waveform showing a sequence of voltage pulses with a pulse width defined for each pulse, according to embodiments.

FIG. 9 illustrates a pulsed voltage waveform in the form of a sequence of rectangular double pulses, with each pulse, such as the pulse (900) being associated with a pulse width or duration. The pulse width/duration may be about 0.5 microseconds, about 1 microsecond, about 5 microseconds, about 10 microseconds, about 25 microseconds, about 50 microseconds, about 100 microseconds, about 125 microseconds, about 140 microseconds, about 150 microseconds, including all values and sub-ranges in between. The pulsed waveform of FIG. 9 illustrates a set of monophasic pulses where the polarities of all the pulses are the same (all positive in FIG. 9, as measured from a zero baseline). In some embodiments, such as for irreversible electroporation applications, the height of each pulse (900) or the voltage amplitude of the pulse (900) may be in the range from about 400 V, about 1,000 V, about 5,000 V, about 10,000 V, about 15,000 V, including all values and sub ranges in between. As illustrated in FIG. 9, the pulse (900) is separated from a neighboring pulse by a time interval (902), also sometimes referred to as a first time interval. The first time interval may be about 10 microseconds, about 50 microseconds, about 100 microseconds, about 200 microseconds, about 500 microseconds, about 800 microseconds, about 1 millisecond including all values and sub ranges in between, in order to generate irreversible electroporation.

Figure 10:
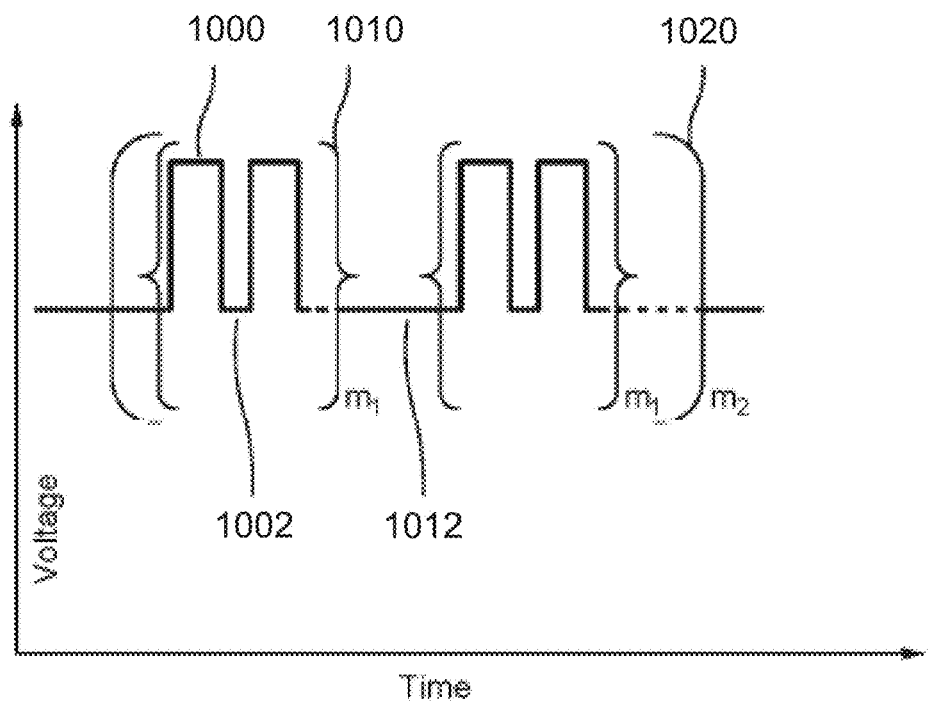
FIG. 10 schematically illustrates a hierarchy of pulses showing pulse widths, intervals between pulses, and groupings of pulses, according to embodiments.

FIG. 10 introduces a pulse waveform with the structure of a hierarchy of nested pulses. FIG. 10 shows a series of monophasic pulses such as pulse (1000) with pulse width/pulse time duration w, separated by a time interval (also sometimes referred to as a first time interval) such as (1002) of duration $t_1$ between successive pulses, a number $m_1$ of which are arranged to form a group of pulses (1010) (also sometimes referred to as a first set of pulses). Furthermore, the waveform has a number $m_2$ of such groups of pulses (also sometimes referred to as a second set of pulses) separated by a time interval (1012) (also sometimes referred to as a second time interval) of duration $t_2$ between successive groups. The collection of $m_2$ such pulse groups, marked by (1020) in FIG. 10, constitutes the next level of the hierarchy, which may be referred to as a packet and/or as a third set of pulses. The pulse width and the time interval $t_1$ between pulses may both be in the range of microseconds to hundreds of microseconds, including all values and sub ranges in between. In some embodiments, the time interval $t_2$ may be at least three times larger than the time interval $t_1$. In some embodiments, the ratio $t_2/t_1$ may be in the range between about 3 and about 300, including all values and sub-ranges in between.

Figure 11:
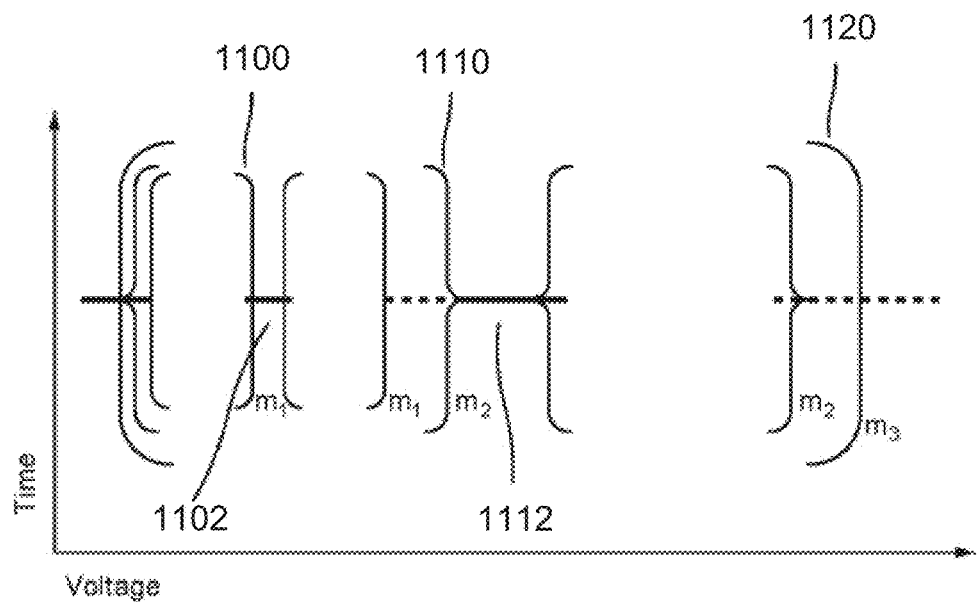
FIG. 11 provides a schematic illustration of a nested hierarchy of monophasic pulses displaying different levels of nested hierarchy, according to embodiments.

FIG. 11 further elaborates the structure of a nested pulse hierarchy waveform. In this figure, a series of $m_1$ pulses (individual pulses not shown) form a group of pulses (1102) (e.g., a first set of pulses). A series of $m_2$ such groups separated by an inter-group time interval (1110) of duration $t_2$ (e.g., a second time interval) between one group and the next form a packet (1110) (e.g., a second set of pulses). A series of $m_3$ such packets separated by time intervals (1112) of duration $t_3$ (e.g., a third time interval) between one packet and the next form the next level in the hierarchy, a super-packet labeled (1120) (e.g., a third set of pulses) in the figure. In some embodiments, the time interval $t_3$ may be at least about thirty times larger than the time interval $t_2$. In some embodiments, the time interval $t_3$ may be at least fifty times larger than the time interval $t_2$. In some embodiments, the ratio $t_3/t_2$ may be in the range between about 30 and about 800, including all values and sub-ranges in between. The amplitude of the individual voltage pulses in the pulse hierarchy may be anywhere in the range from 500 V to 7,000 V or higher, including all values and sub-ranges in between.

Figure 12:
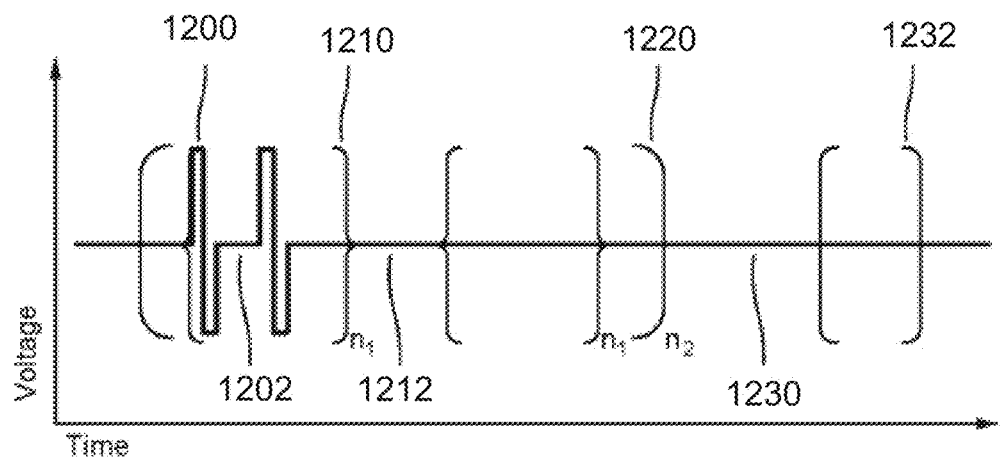
FIG. 12 is a schematic illustration of a nested hierarchy of biphasic pulses displaying different levels of nested hierarchy, according to embodiments.

FIG. 12 provides an example of a biphasic waveform sequence with a hierarchical structure. In the example shown in the figure, biphasic pulses (1200) have a positive voltage portion as well as a negative voltage portion to complete one cycle of the pulse. There is a time delay (1202) (e.g., a first time interval) between adjacent cycles of duration $t_1$, and $n_1$ such cycles form a group of pulses (1210) (e.g., a first set of pulses). A series of $n_2$ such groups separated by an inter-group time interval (1212) (e.g., a second time interval) of duration $t_2$ between one group and the next form a packet (1220) (e.g., a second set of pulses). The figure also shows a second packet (1232), with a time delay (1230) (e.g., a third time interval) of duration $t_3$ between the packets. Just as for monophasic pulses, higher levels of the hierarchical structure may be formed as well. The amplitude of each pulse or the voltage amplitude of the biphasic pulse may be anywhere in the range from 500 V to 7,000 V or higher, including all values and sub-ranges in between. The pulse width/pulse time duration may be in the range from nanoseconds or even sub-nanoseconds to tens of microseconds, while the delays $t_1$ may be in the range from zero to several microseconds. The inter-group time interval $t_2$ may be at least ten times larger than the pulse width. In some embodiments, the time interval $t_3$ may be at least about twenty times larger than the time interval $t_2$. In some embodiments, the time interval $t_3$ may be at least fifty times larger than the time interval $t_2$.

Embodiments disclosed herein may include waveforms structured as hierarchical waveforms that include waveform elements/pulses at various levels of the hierarchy. The individual pulses such as pulse (1000) in FIG. 10 may include the first level of the hierarchy, and have an associated pulse time duration and a first time interval between successive pulses. A set of pulses, or elements of the first level structure, form a second level of the hierarchy such as the group of pulses/second set of pulses (1010) in FIG. 10. Among other parameters associated with the waveform are parameters such as a total time duration of the second set of pulses (not shown), a total number of first level elements/first set of pulses, and second time intervals between successive first level elements that describe the second level structure/second set of pulses. In some embodiments, the total time duration of the second set of pulses may be between about 20 microseconds and about 10 milliseconds, including all values and sub-ranges in between. A set of groups, second set of pulses, or elements of the second level structure, form a third level of the hierarchy such as the packet of groups/third set of pulses (1020) in FIG. 10. Among other parameters, there is a total time duration of the third set of pulses (not shown), a total number of second level elements/second set of pulses, and third time intervals between successive second level elements that describe the third level structure/third set of pulses. In some embodiments, the total time duration of the third set of pulses may be between about 60 microseconds and about 200 milliseconds, including all values and sub-ranges in between. The generally iterative or nested structure of the waveforms may continue to a higher plurality of levels, such as ten levels of structure, or more.

In some embodiments, hierarchical waveforms with a nested structure and hierarchy of time intervals as described herein may be useful for irreversible electroporation ablation energy delivery, providing a good degree of control and selectivity for applications in different tissue types. A variety of hierarchical waveforms may be generated with a suitable pulse generator of the type described in this disclosure. It is understood that while the examples herein identify separate monophasic and biphasic waveforms for clarity, it should be noted that combination waveforms, where some portions of the waveform hierarchy are monophasic while other portions are biphasic, may also be generated/implemented.

Figure 13:
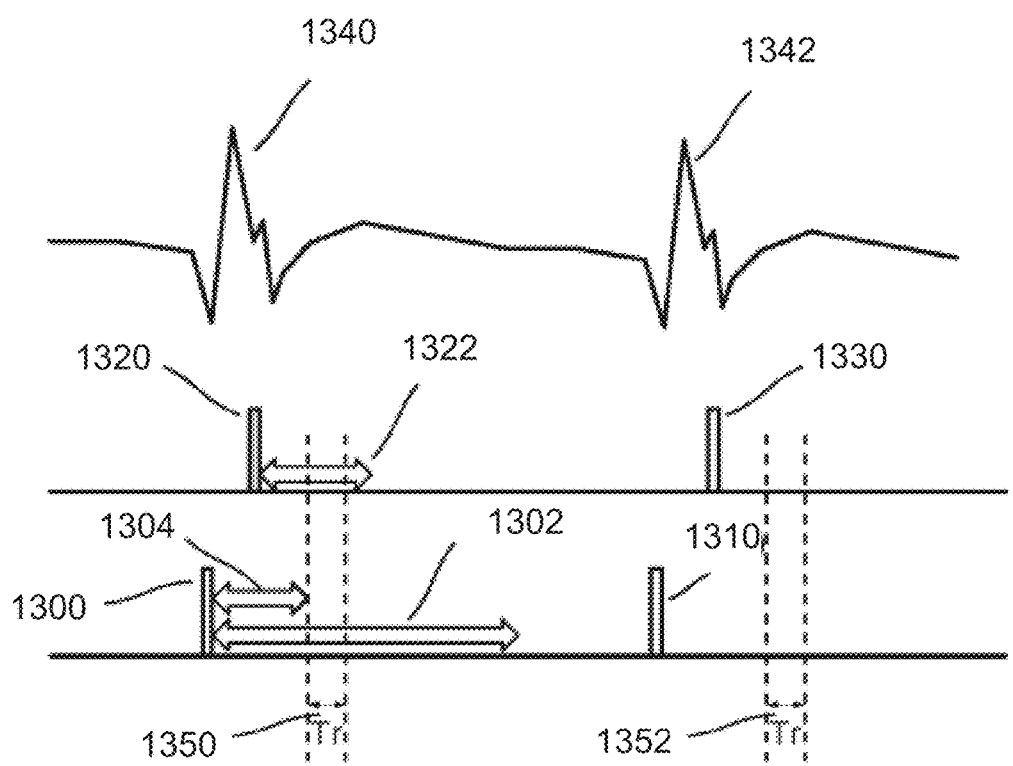
FIG. 13 illustrates schematically a time sequence of electrocardiograms and cardiac pacing signals together with atrial and ventricular refractory time periods and indicating a time window for irreversible electroporation ablation, according to embodiments.

In some embodiments, the ablation pulse waveforms described herein may be applied during the refractory period of the cardiac cycle so as to avoid disruption of the sinus rhythm of the heart. In some embodiments, a method of treatment may include electrically pacing the heart with a cardiac stimulator (e.g., cardiac stimulator (150)) to ensure pacing capture to establish periodicity and predictability of the cardiac cycle, and then defining a time window within the refractory period of the cardiac cycle within which one or more pulsed ablation waveforms may be delivered. FIG. 13 illustrates an example where both atrial and ventricular pacing is applied (for instance, with pacing leads or catheters situated in the right atrium and right ventricle respectively). With time represented on the horizontal axis, FIG. 13 illustrates a series of ventricular pacing signals (1300, 1310), and a series of atrial pacing signals (1320, 1330), along with a series of ECG waveforms (1340, 1342) that are driven by the pacing signals. As indicated in FIG. 13 by the thick arrows, there is an atrial refractory time window (1322) and a ventricular refractory time window (1302) that respectively follow the atrial pacing signal (1322) and the ventricular pacing signal (1300). As shown in FIG. 13, a common refractory time window (1350) of duration $T_r$ may be defined that lies within both atrial and ventricular refractory time windows (1322, 1302). In some embodiments, the electroporation ablation waveform(s) may be applied in this common refractory time window (1350). The start of this refractory time window (1322) is offset from the pacing signal (1300) by a time offset (1304) as indicated in FIG. 13. The time offset (1304) may be smaller than about 25 milliseconds, in some embodiments. At the next heartbeat, a similarly defined common refractory time window (1352) is the next time window available for application of the ablation waveform(s). In this manner, the ablation waveform(s) may be applied over a series of heartbeats, at each heartbeat remaining within the common refractory time window. In one embodiment, each packet of pulses as defined above in the pulse waveform hierarchy may be applied over a heartbeat, so that a series of packets is applied over a series of heartbeats, for a given electrode set. Similarly, a first waveform packet may be delivered successively over a first sequence of electrodes, followed by a second waveform packet delivered over a second sequence of electrodes, and so on; in some cases, it may even be convenient for the second sequence of electrodes to be different from the second sequence of electrodes. The architecture of the signal generator and routing console as disclosed herein permits the delivery of a variety of such hierarchical waveforms wherein waveform packet delivery to a given set of electrodes, in the sense disclosed herein, may be interspersed with waveform packet deliveries to a different set of electrodes. This modality of interspersed waveform delivery described herein may include monophasic, biphasic, and mixed pulses that include both monophasic and biphasic components.

It is understood that while the examples herein identify separate monophasic and biphasic waveforms, it should be appreciated that combination waveforms, where some portions of the waveform hierarchy are monophasic while other portions are biphasic, may also be generated. A voltage pulse waveform having a hierarchical structure may be applied across different anode-cathode subsets (optionally with a time delay). As discussed above, one or more of the waveforms applied across the anode-cathode subsets may be applied during the refractory period of a cardiac cycle. It should be appreciated that the method steps described herein may be combined and modified as appropriate. Likewise, while the examples of electrode channel selection disclosed herein describe the selection of one anode and two cathode channels, it should be clear that a wide variety of channels may be selected to act as anodes or cathodes, without limitation.

As used herein, the terms "about" and/or "approximately" when used in conjunction with numerical values and/or ranges generally refer to those numerical values and/or ranges near to a recited numerical value and/or range. In some instances, the terms "about" and "approximately" may mean within ±10% of the recited value. For example, in some instances, "about 100 [units]" may mean within ±10% of 100 (e.g., from 90 to 110). The terms "about" and "approximately" may be used interchangeably.

Some embodiments described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs); Compact Disc-Read Only Memories (CD-ROMs), and holographic devices; magneto-optical storage media such as optical disks; solid state storage devices such as a solid state drive (SSD) and a solid state hybrid drive (SSHD); carrier wave signal processing modules; and hardware devices that are specially configured to store and execute program code, such as Application-Specific Integrated Circuits (ASICs), Programmable Logic Devices (PLDs), Read-Only Memory (ROM), and Random-Access Memory (RAM) devices. Other embodiments described herein relate to a computer program product, which may include, for example, the instructions and/or computer code disclosed herein.

The systems, devices, and/or methods described herein may be performed by software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware) may be expressed in a variety of software languages (e.g., computer code), including C, C++, Java®, Python, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

In some embodiments, the systems, devices, and methods may be in communication with other computing devices (not shown) via, for example, one or more networks, each of which may be any type of network (e.g., wired network, wireless network). A wireless network may refer to any type of digital network that is not connected by cables of any kind. Examples of wireless communication in a wireless network include, but are not limited to cellular, radio, satellite, and microwave communication. However, a wireless network may connect to a wired network in order to interface with the Internet, other carrier voice and data networks, business networks, and personal networks. A wired network is typically carried over copper twisted pair, coaxial cable and/or fiber optic cables. There are many different types of wired networks including wide area networks (WAN), metropolitan area networks (MAN), local area networks (LAN), Internet area networks (IAN), campus area networks (CAN), global area networks (GAN), like the Internet, and virtual private networks (VPN). Hereinafter, network refers to any combination of wireless, wired, public and private data networks that are typically interconnected through the Internet, to provide a unified networking and information access system.

Cellular communication may encompass technologies such as GSM, PCS, CDMA or GPRS, W-CDMA, EDGE or CDMA2000, LTE, WiMAX, and 5G networking standards. Some wireless network deployments combine networks from multiple cellular networks or use a mix of cellular, Wi-Fi, and satellite communication. In some embodiments, the systems, devices, and methods described herein may include a radiofrequency receiver, transmitter, and/or optical (e.g., infrared) receiver and transmitter to communicate with one or more devices and/or networks.

The specific examples and descriptions herein are exemplary in nature and embodiments may be developed by those skilled in the art based on the material taught herein without departing from the scope of the present invention, which is limited only by the attached claims.

We claim:

1. A system, comprising:
   a set of electrodes; and
   a signal generator configured to couple to the set of electrodes during use, the signal generator including:
   a routing console;
   a set of electrode channels coupled to the routing console, each electrode channel of the set of electrode channels corresponding to an electrode of the set of electrodes, each electrode channel including a first electronic switch configured to switch between an ON state and an OFF state; and
   a second electronic switch configured to switch between an ON state and an OFF state;
   an energy source coupled to the set of electrode channels; and
   a processor coupled to the set of electrode channels and to the routing console, the processor configured to selectively define a first sequence of subsets of one or more electrode channels of the set of electrode channels as an anode sequence and to selectively define a second sequence of subsets of one or more electrode channels of the set of electrode channels as a cathode sequence,
   the routing console configured to selectively couple the set of electrodes during use and including a first drive circuit coupled to the first electronic switch to control the state of the first electronic switch, and a second drive circuit coupled to the second electronic switch to control the state of the second electronic switch; and
   the processor, the routing console and the energy source collectively configured to deliver a pulse waveform to the set of electrodes in a time-sequenced fashion by pairing respective electrode channels of the first sequence of electrode channels and second sequence of electrode channels, wherein the signal generator further includes a sensing circuit coupled to the set of electrode channels and to the processor, wherein the processor, the routing console and the energy source are collectively configured to deliver the pulse waveform to the set of electrodes at a first time, the processor and the sensing circuit further configured, at a second time prior to the first time and for each electrode channel of the set of electrode channels to conduct a fault test, including:
setting the first electronic switch to the ON state;
setting the second electronic switch to the OFF state; and
classifying that electrode channel as passing the fault test when substantially no current is detected by the sensing circuit.

2. The system of claim 1, the processor further configured to configure the first sequence as an anode by setting the first electronic switch of the first electrode channel to the ON state and by setting the second electronic switch of the first sequence to the OFF state,
the processor further configured to configure the second sequence as a cathode by setting the first electronic switch of the second sequence to the OFF state and by setting the second electronic switch of the second sequence to the ON state.

3. The system of claim 1, each of the electronic switches selected from the group consisting of bipolar junction transistors, bipolar Field Effect transistors (Bi-FET's), power Metal Oxide Semiconductor Field Effect Transistors (MOSFET's), and Insulated-Gate Bipolar Transistors (IGBT's).

4. The system of claim 1, wherein the fault test is a first fault test, the processor and the sensing circuit further configured, at the second time prior to the first time and for each electrode channel of the set of electrode channels:
to conduct a second fault test, including:
setting the first electronic switch to the OFF state;
setting the second electronic switch to the ON state; and
classifying that electrode channel as passing the second fault test when substantially no current is detected by the sensing circuit; and
to conduct a third fault test, including:
setting the first electronic switch to the ON state;
setting the second electronic switch to the ON state; and
classifying that electrode channel as passing the third fault test when a predetermined amount of current is detected by the sensing circuit; and
classifying that electrode channel as working without fault when that electrode channel passes the first fault test, the second fault test, and the third fault test.

5. The system of claim 1, the signal generator further including:
a resistive element coupled to the set of electrode channels; and
a sensing circuit coupled to the resistive element, the routing console, and to the processor,
wherein the processor and the energy source are collectively configured to deliver the pulse waveform to the set of electrodes at a first time, the processor and the sensing circuit further configured, at a second time subsequent to the first time and for each electrode channel of the set of electrode channels:
to set the first electronic switch to the ON state and set the second electronic switch to the ON state for a predetermined duration of time to at least partially discharge the energy source.

6. The system of claim 1, the sensing circuit further configured to detect arcing during use.

7. The system of claim 1, further comprising an ablation device that includes the set of electrodes as a linear array of N electrodes, the set of electrode channels including N electrode channels corresponding to the N electrodes,
wherein the first sequence of subsets of electrode channels includes an electrode channel corresponding to a first electrode in the linear array of N electrodes, and wherein the second sequence of subsets of electrode channels comprises only electrode channels that do not correspond to any electrodes adjacent to the first electrode in the linear array of N electrodes.

8. The system of claim 1, wherein a given electrode channel is in the first sequence of subsets at a first time, and is in the second sequence of subsets at a second time subsequent to the first time.

9. The system of claim 1, wherein a given subset of electrode channels in the first sequence of subsets and its corresponding subset of electrode channels in the second sequence of subsets are each configured as a half bridge amplifier, and wherein the combination of the given subset of electrode channels and its corresponding subset of electrode channels is collectively configured as a full bridge amplifier.

10. The system of claim 1, the pulse waveform including:
a first level of a hierarchy of the pulse waveform including a first set of pulses, each pulse having a pulse time duration, a first time interval separating successive pulses;
a second level of the hierarchy of the pulse waveform including a plurality of first sets of pulses as a second set of pulses, a second time interval separating successive first sets of pulses, the second time interval being at least three times the duration of the first time interval; and
a third level of the hierarchy of the pulse waveform including a plurality of second sets of pulses as a third set of pulses, a third time interval separating successive second sets of pulses, the third time interval being at least thirty times the duration of the second level time interval.

11. The system of claim 1, further comprising a cardiac stimulator configured to generate a pacing signal for cardiac stimulation during use, the cardiac stimulator communicably coupled to the signal generator and further configured to transmit an indication of the pacing signal to the signal generator,
the processor of the signal generator further configured to generate the pulse waveform in synchronization with the indication of the pacing signal, where the synchronization includes a pre-determined offset.

12. The system of claim 1, wherein the processor and the sensing circuit are further configured to partially discharge the energy source over a plurality of discharge cycles, wherein each discharge cycle includes partial discharge of each electrode channel of the set of electrode channels.

13. A generator, comprising:
a routing console configured to couple a set of electrodes during use;
a set of electrode channels coupled to the routing console, each electrode channel of the set of electrode channels corresponding to an electrode of the set of electrodes, each electrode channel including:
a first electronic switch configured to switch between an ON state and an OFF state;

a first drive circuit coupled to the first electronic switch to control the state of the first electronic switch;

a second electronic switch configured to switch between an ON state and an OFF state;

a second drive circuit coupled to the second electronic switch to control the state of the second electronic switch;

an energy source coupled to the set of electrode channels; and a processor coupled to the energy source, the set of electrode channels, and the drive circuit, the processor configured to:

set one or more first electrode channels of the set of electrode channels as an anode; and set one or more second electrode channels of the set of electrode channels as a cathode, the processor, the routing console, and the energy source collectively configured to deliver a pulse waveform to the set of electrodes during use via the one or more first electrode channels and the one or more second electrode channels, and wherein each pulse of the pulse waveform is a substantially DC pulse, wherein the signal generator further includes a sensing circuit coupled to the set of electrode channels and to the processor, wherein the processor and the energy source are collectively configured to deliver the pulse waveform to the set of electrodes at a first time, the processor and the sensing circuit collectively configured, at a second time prior to the first time and for each electrode channel of the set of electrode channels:

to conduct a first fault test, including:

setting the first electronic switch to the ON state;

setting the second electronic switch to the OFF state; and classifying that electrode channel as passing the first fault test when substantially no current is detected by the sensing circuit; and to conduct a second fault test, including:

setting the first electronic switch to the OFF state;

setting the second electronic switch to the ON state; and classifying that electrode channel as passing the second fault test when substantially no current is detected by the sensing circuit.

14. The generator of claim 13, the processor further configured to configure each first electrode channel as an anode by setting the first electronic switch of that electrode channel to the ON state and by setting the second electronic switch of the first electrode channel to the OFF state, the processor further configured to configure each second electrode channel as a cathode by setting the first electronic switch of that second electrode channel to the OFF state and by setting the second electronic switch of that second electrode channel to the ON state.

15. The generator of claim 13, the processor and the sensing circuit collectively configured, at the second time prior to the first time and for each electrode channel of the set of electrode channels to conduct a third fault test, including:

setting the first electronic switch to the ON state;

setting the second electronic switch to the ON state; and classifying that electrode channel as passing the third fault test when a predetermined amount of current is detected by the sensing circuit; and classifying that electrode channel as working without fault when that electrode channel passes the first fault test, the second fault test, and the third fault test.

16. The generator of claim 13, the signal generator further including a resistive element coupled to the set of electrode channels and to the sensing circuit, wherein the processor and the energy source are configured to deliver the pulse waveform to the set of electrodes at a first time, the processor and the sensing circuit further configured, at a second time subsequent to the first time and for each electrode channel of the set of electrode channels:

to set the first electronic switch to the ON state and set the second electronic switch to the ON state for a predetermined duration of time to at least partially discharge the energy source.

17. The generator of claim 13, wherein the processor and the energy source are collectively configured to deliver the pulse waveform to the set of electrodes at a first time, the processor further configured to, at a second time subsequent to the first time:

configure one of the first electrode channels of the set of electrode channels as a cathode; and configure one of the second electrode channels of the set of electrode channels as an anode, the processor and the energy source further collectively configured to deliver the pulse waveform to the set of electrodes at the second time.

18. The generator of claim 13, wherein the one or more first electrode channels and the one or more second electrode channels are configured as a half bridge amplifier, and wherein the combination of one or more of the first electrode channels and one or more of the second electrode channels is collectively configured as a full bridge amplifier.

19. The generator of claim 13, the pulse waveform including:

a first level of a hierarchy of the pulse waveform including a first set of pulses, each pulse having a pulse time duration, a first time interval separating successive pulses;

a second level of the hierarchy of the pulse waveform including a plurality of first sets of pulses as a second set of pulses, a second time interval separating successive first sets of pulses, the second time interval being at least three times the duration of the first time interval; and a third level of the hierarchy of the pulse waveform including a plurality of second sets of pulses as a third set of pulses, a third time interval separating successive second sets of pulses, the third time interval being at least thirty times the duration of the second level time interval.

20. A system, comprising:

a set of electrodes; and a signal generator configured to couple to the set of electrodes during use, the signal generator including:

a routing console;

a set of electrode channels coupled to the routing console, each electrode channel of the set of electrode channels corresponding to an electrode of the set of electrodes, each electrode channel including a first electronic switch and a second electronic switch, both switches configured to switch between an ON state and an OFF state;

an energy source coupled to the set of electrode channels; and a processor coupled to the set of electrode channels and to the routing console, the processor configured to selectively define a first sequence of subsets of one or more electrode channels of the set of electrode channels as an anode sequence and to selectively define a second sequence of subsets of one or more electrode channels of the set of electrode channels as a cathode sequence;

a resistive element coupled to the set of electrode channels; and a sensing circuit coupled to the resistive element, the routing console and to the processor, the routing console configured to selectively couple the set of electrodes during use and including a first drive circuit coupled to the first electronic switch to control the state of the first electronic switch and a second drive circuit coupled to the second electronic switch to control the state of the second electronic switch; and the processor, the routing console, and the energy source collectively configured to deliver a pulse waveform to the set of electrodes in a time-sequenced fashion by pairing respective electrode channels of the first sequence of electrode channels and second sequence of electrode channels, wherein at a time subsequent to the pulsed waveform delivery, and for each electrode channel of the set of electrode channels, the first electronic switch is set to the ON state and the second electronic switch is set to the ON state for a predetermined duration of time to at least partially discharge the energy source, wherein the signal generator further includes a sensing circuit coupled to the set of electrode channels and to the processor, wherein the processor, the routing console and the energy source are collectively configured to deliver the pulse waveform to the set of electrodes at a first time, the processor and the sensing circuit further configured, at a second time prior to the first time and for each electrode channel of the set of electrode channels:

to conduct a first fault test, including:
setting the first electronic switch to the ON state;
setting the second electronic switch to the OFF state; and
classifying that electrode channel as passing the first fault test when substantially no current is detected by the sensing circuit;

to conduct a second fault test, including:
setting the first electronic switch to the ON state;
setting the second electronic switch to the ON state; and
classifying that electrode channel as passing the second fault test when a predetermined amount of current is detected by the sensing circuit.

21. The system of claim 20, wherein the first and second electronic switches of each electrode channel comprise insulated gate bipolar transistors.

22. The system of claim 20, the processor and the sensing circuit further configured, at the second time prior to the first time and for each electrode channel of the set of electrode channels to conduct a third fault test, including:
setting the first electronic switch to the OFF state;
setting the second electronic switch to the ON state; and
classifying that electrode channel as passing the third fault test when substantially no current is detected by the sensing circuit; and
classifying that electrode channel as working without fault when that electrode channel passes the first fault test, the second fault test, and the third fault test.

* * * * *